US010457646B1

(12) United States Patent
Cai et al.

(10) Patent No.: US 10,457,646 B1
(45) Date of Patent: Oct. 29, 2019

(54) HYDANTOIN DERIVATIVE COMPOUNDS, METHODS OF USE AND METHODS OF TREATMENT

(71) Applicants: Jianfeng Cai, Tampa, FL (US); Ma Su, Tampa, FL (US); Alekhya Nimmagadda, Tampa, FL (US); Peng Teng, Tampa, FL (US)

(72) Inventors: Jianfeng Cai, Tampa, FL (US); Ma Su, Tampa, FL (US); Alekhya Nimmagadda, Tampa, FL (US); Peng Teng, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/823,667

(22) Filed: Nov. 28, 2017

Related U.S. Application Data

(60) Provisional application No. 62/426,698, filed on Nov. 28, 2016.

(51) Int. Cl.
 *C07D 233/72* (2006.01)
(52) U.S. Cl.
 CPC .................. *C07D 233/72* (2013.01)
(58) Field of Classification Search
 CPC ..................................... C07D 233/72
 See application file for complete search history.

(56) References Cited

PUBLICATIONS

Levy, S. B.; Marshall, B. Antibacterial resistance worldwide: causes, challenges and responses. Nat. Med. 2004, S122-129.
Niku-Paavola, M. L.; Laitila, A.; Mattila-Sandholm, T.; Haikara, A. New types of antimicrobial compounds produced by lactobacillus plantarum. J. Appl. Microbiol. 1999, 86, 29-35.
Hidayat, Ika-Wiani, H.; Yee Yee, T.; David St, C. B.; Roger, W. R. Biological evaluation of certain substituted hydantoins and benzalhydantoins against microbes. IOP Conf. Ser.: Mater. Sci. Eng. 2016, 107, 012058.
Fujisaki, F.; Toyofuku, K.; Egami, M.; Ishida, S.; Nakamoto, N.; Kashige, N.; Miake, F.; Sumoto, K. Antibacterial activity of some 5-dialkylaminomethylhydantoins and related derivatives. Chem. Pharm. Bull. 2013, 61, 1090-1093.
Szymanska, E.; Kiec-Kononowicz, K.; Bialecka, A.; Kasprowicz, A. Antimicrobial activity of 5-arylidene aromatic derivatives of hydantoin. Part 2. Farmaco 2002, 57, 39-44.
Van der Stelt, C.; Hofman, P. S.; Nauta, W. T. The effect of alkyl substitution in drugs. 18. Investigation into the synthesis and antimicrobial properties of 1-[(5-nitrofurfurylidene)amino]hydantoin and its 3-substituted products. A Arzneimittelforschung 1967, 17, 1331-1333.
Tu, Y.; McCalla, D. R. Effect of nitrofurazone on bacterial RNA and ribosome synthesis and on the function of ribosomes. Chem. Biol. Interact. 1976, 14, 81-91.
Tu, Y.; McCalla, D. R. Effect of activated nitrofurans on DNA. Biochimi. Biophys. Acta 1975, 402, 142-149.
McOsker, C. C.; Fitzpatrick, P. M. Nitrofurantoin: mechanism of action and implications for resistance development in common uropathogens. J. Antimicrob. Chemother. 1994, 33, 23-30.
Ge, Y.; MacDonald, D. L.; Holroyd, K. J.; Thomsberry, C.; Wexler, H.; Zasloff, M. In vitro antibacterial properties of pexiganan, an analog of magainin. Antimicrob. Agents Chemother. 1999, 43, 782-788.
Zhanel, G. G.; Hoban, D. J.; Karlowsky, J. A. Nitrofurantoin is active against vancomycin-resistant enterococci. Antimicrob. Agents Chemother. 2001, 45, 324-326.
Yu, H.; Pan, L.; Li, P.; Zhang, K.; Lin, X.; Zhang, Y.; Tang, X. Nitrofurantoin enteric pellets with high bioavailability based on aciform crystalline formation by wet milling. Pharm. Dev. Technol. 2015, 20, 433-441.
Topcu, Y.; Tufan, F.; Bahat, G.; Karan, A. Nitrofurantoin and older women. Can. Med. Assoc. J. 2015, 187, 1236.
Singh, N.; Gandhi, S.; McArthur, E.; Moist, L.; Jain, A. K.; Liu, A. R.; Sood, M. M.; Garg, A. X. Kidney function and the use of nitrofurantoin to treat urinary tract infections in older women. Can. Med. Assoc. J. 2015, 187, 648-656.
Zykov, I. N.; Sundsfjord, A.; Smabrekke, L; Samuelsen, O. The antimicrobial activity of mecillinam, nitrofurantoin, temocillin and fosfomycin and comparative analysis of resistance patterns in a nationwide collection of ESBL-producing *Escherichia coli* in Norway 2010-2011. Infect. Dis. (Lond) 2016, 48 (2), 99-107.
Price, J. R.; Guran, L. A.; Gregory, W. T.; McDonagh, M. S. Nitrofurantoin vs other prophylactic agents in reducing recurrent urinary tract infections in adult women: a systematic review and meta-analysis. J. Obstet. Gynecol. 2016, 15, 548-560.
McKinnell, J. A.; Stollenwerk, N. S.; Jung, C. W.; Miller, L. G. Nitrofurantoin compares favorably to recommended agents as empirical treatment of uncomplicated urinary tract infections in a decision and cost analysis. Mayo. Clin. Proc. 2011, 86, 480-488.
Garau, J. Other antimicrobials of interest in the era of extended-spectrum beta-lactamases: fosfomycin, nitrofurantoin and tigecycline. Clin. Microbiol. Infect. 2008, 14, 198-202.
Otreebska-Machaj, E.; Chevalier, J.; Handzlik, J.; Szymanska, E.; Schabikowski, J.; Boyer, G.; Bolla, J. M.; Kiec-Kononowicz, K.; Pages, J. M.; Alibert, S. Efflux pump blockers in gram-negative bacteria: the new generation of hydantoin based-modulators to improve antibiotic activity. Front. Microbiol. 2016, 7, 622.
Marinova, P.; Marinov, M.; Kazakova, M.; Feodorova, Y.; Slavchev, A.; Blazheva, D.; Georgiev, D.; Penchev, P.; Sarafian, V.; Stoyanov, N. Study on the synthesis, characterization and bioactivities of 3-methyl-9'-fluorenespiro-5-hydantoin. Acta. Chim. Slov. 2016, 63, 26-32.
Handzlik, J.; Szymanska, E.; Chevalier, J.; Otrebska, E.; Kiec-Kononowicz, K.; Pages, J. M.; Alibert, S. Amine-alkyl derivatives of hydantoin: new tool to combat resistant bacteria. Eur. J. Med. Chem. 2011, 46, 5807-5816.

(Continued)

*Primary Examiner* — Rebecca L Anderson
(74) *Attorney, Agent, or Firm* — Thomas | Horstemeyer, LLP

(57) ABSTRACT

The present disclosure provides compositions including a hydantoin derivative compound, pharmaceutical compositions including a hydantoin derivative compound, methods of treatment of a condition (e.g., bacterial infection) or disease, methods of treatment using compositions or pharmaceutical compositions, and the like.

12 Claims, 6 Drawing Sheets

(56) References Cited

PUBLICATIONS

Marr, A. K.; Gooderham, W. J.; Hancock, R. E. Antibacterial peptides for therapeutic use: obstacles and realistic outlook. Curr. Opin. Pharmacol. 2006, 6, 468-472.

Hancock, R. E.; Sahl, H. G. Antimicrobial and host-defense peptides as new anti-infective therapeutic strategies. Nat. Biotechnol. 2006, 24, 1551-1557.

Liu, R. H.; Chen, X. Y.; Falk, S. P.; Mowery, B. P.; Karlsson, A. J.; Weisblum, B.; Palecek, S. P.; Masters, K. S.; Gellman, S. H. Structure-activity relationships among antifungal nylon-3 polymers: identification of materials active against drug-resistant strains of candida albicans. J. Am. Chem. Soc. 2014, 136, 4333-4342.

Choi, H.; Chakraborty, S.; Liu, R. H.; Gellman, S. H.; Weisshaar, J. C. Medium effects on minimum inhibitory concentrations of nylon-3 polymers against *E-coli*. PloS One 2014, 9, e104500.

Raguse, T. L.; Porter, E. A.; Weisblum, B.; Gellman, S. H. Structure-activity studies of 14-helical antimicrobial beta-peptides: probing the relationship between conformational stability and antimicrobial potency. J. Am. Chem. Soc. 2002, 124, 12774-12785.

Violette, A.; Fournel, S.; Lamour, K.; Chaloin, O.; Frisch, B.; Briand, J. P.; Monteil, H.; Guichard, G. Mimicking helical antibacterial peptides with nonpeptidic folding oligomers. Chem. Biol. 2006, 13, 531-538.

Kapoor, R.; Eimerman, P. R.; Hardy, J. W.; Cirillo, J. D.; Contag, C. H.; Barron, A. E. Efficacy of antimicrobial peptoids against Mycobacterium tuberculosis. Antimicrob. Agents Chemother. 2011, 55 (6), 3058-3062.

Ghosh, C.; Manjunath, G. B.; Akkapeddi, P.; Yarlagadda, V.; Hogue, J.; Uppu, D. S.; Konai, M. M.; Haldar, J. Small molecular antibacterial peptoid mimics: the simpler the better! J. Med. Chem. 2014, 57, 1428-1436.

Teng, P.; Shi, Y.; Sang, P.; Cai, J. y-AApeptides as a new class of peptidomimetics. Chem.—Eur. J. 2016, 22, 5458-5466.

Shi, Y.; Teng, P.; Sang, P.; She, F.; Wei, L.; Cai, J. y-AApeptides: design, structure, and applications. Acc. Chem. Res. 2016, 49, 428-441.

Fjell, C. D.; Hiss, J. A.; Hancock, R. E. W.; Schneider, G. Designing antimicrobial peptides: form follows function. Nat. Rev. Drug Discov. 2012, 11, 37-51.

Hancock, R. E. W.; Brown, K. L.; Mookherjee, N. Host defence peptides from invertebrates—emerging antimicrobial strategies. Immunobiology 2006, 211, 315-322.

Brown, K. L.; Hancock, R. E. W. Cationic host defense (antimicrobial) peptides. Curr. Opin. Immunol. 2006, 18, 24-30.

Choi, S.; Isaacs, A.; Clements, D.; Liu, D.; Kim, H.; Scott, R. W.; Winkler, J. D.; DeGrado, W. F. De novo design and in vivo activity of conformationally restrained antimicrobial arylamide foldamers. Proc. Natl. Acad. Sci. U. S. A. 2009, 106, 6968-6973.

Chongsiriwatana, N. P.; Patch, J. A.; Czyzewski, A. M.; Dohm, M. T.; Ivankin, A.; Gidalevitz, D.; Zuckermann, R. N.; Barron, A. E. Peptoids that mimic the structure, function, and mechanism of helical antimicrobial peptides. Proc. Natl. Acad. Sci. U. S. A. 2008, 105, 2794-2799.

Wu, G.; Abraham, T.; Rapp, J.; Vastey, F.; Saad, N.; Balmir, E. Daptomycin: evaluation of a high-dose treatment strategy. Int. J. Antimicrob. Agents 2011, 38, 192-196.

Muraih, J. K.; Pearson, A.; Silverman, J.; Palmer, M. Oligomerization of daptomycin on membranes. Biochim. Biophys. Acta 2011, 1808, 1154-1160.

Yahav, D.; Farbman, L.; Leibovici, L.; Paul, M. Colistin: new lessons on an old antibiotic. Clin. Microbiol. Infect. 2012, 18, 18-29.

Nation, R. L.; Li, J. Colistin in the 21st century. Curr. Opin. Infect. Dis. 2009, 22, 535-543.

Teng, P.; Huo, D.; Nimmagadda, A.; Wu, J.; She, F.; Su, M.; Lin, X.; Yan, J.; Cao, A.; Xi, C.; Hu, Y.; Cai, J. Small antimicrobial agents based on acylated reduced amide scaffold. J. Med. Chem. 2016, 59, 7877-7887.

Li, Y.; Smith, C.; Wu, H.; Teng, P.; Shi, Y.; Padhee, S.; Jones, T.; Nguyen, A. M.; Cao, C.; Yin, H.; Cai, J. Short antimicrobial lipo-alpha/gamma-AA hybrid peptides. ChemBioChem 2014, 15, 2275-2280.

Padhee, S.; Li, Y.; Cai, J. Activity of lipo-cyclic gamma-AApeptides against biofilms of *Staphylococcus epidermidis* and Pseudomonas aeruginosa. Bioorg. Med. Chem. Lett. 2015, 25, 2565-2569.

Li, Y.; Smith, C.; Wu, H.; Padhee, S.; Manoj, N.; Cardiello, J.; Qiao, Q.; Cao, C.; Yin, H.; Cai, J. Lipidated cyclic y-AApeptides display both antimicrobial and anti-inflammatory activity. ACS Chem. Biol. 2014, 9, 211-217.

Niu, Y.; Padhee, S.; Wu, H.; Bai, G.; Qiao, Q.; Hu, Y.; Harrington, L.; Burda, W. N.; Shaw, L. N.; Cao, C.; Cai, J. Lipo-gamma-AApeptides as a new class of potent and broad-spectrum antimicrobial agents. J. Med. Chem. 2012, 55, 4003-4009.

Hu, Y.; Amin, M. N.; Padhee, S.; Wang, R. E.; Qiao, Q.; Bai, G.; Li, Y.; Mathew, A.; Cao, C.; Cai, J. Lipidated peptidomimetics with improved antimicrobial activity. ACS Med. Chem. Lett. 2012, 3, 683-686.

Wu, H. F.; She, F. Y.; Gao, W. Y.; Prince, A.; Li, Y. Q.; Wei, L. L.; Mercer, A.; Wojtas, L.; Ma, S. Q.; Cai, J. F. The synthesis of head-to-tail cyclic sulfono-gamma-AApeptides. Org. Biomol. Chem. 2015, 13, 672-676.

Wu, H. F.; Teng, P.; Cai, J. F. Rapid access to multiple classes of peptidomimetics from common gamma-AApeptide building blocks. Eur. J. Org. Chem. 2014, 2014, 1760-1765.

Chamberlain, R. E. Chemotherapeutic properties of prominent nitrofurans. J. Antimicrob. Chemother. 1976, 2 (4), 325-336.

Bowdish, D. M. E.; Davidson, D. J.; Lau, Y. E.; Lee, K.; Scott, M. G.; Hancock, R. E. W. Impact of LL-37 on anti-infective immunity. J. Leukoc. Biol. 2005, 77, 451-459.

Rubinstein, E.; Kollef, M. H.; Nathwani, D. Pneumonia caused by methicillin-resistant *Staphylococcus aureus*. Clin. Infect. Dis. 2008, 46, S378-385.

Huo, D.; Ding, J.; Cui, Y. X.; Xia, L. Y.; Li, H.; He, J.; Zhou, Z. Y.; Wang, H. W.; Hu, Y. X-ray CT and pneumonia inhibition properties of gold-silver nanoparticles for targeting MRSA induced pneumonia. Biomaterials 2014, 35, 7032-7041.

Niu, Y.; Hu, Y.; Li, X.; Chen, J.; Cai, J. [gamma]-AApeptides: design, synthesis and evaluation. New J. Chem. 2011, 35, 542-545.

Li, Y.; Wu, H.; Teng, P.; Bai, G.; Lin, X.; Zuo, X.; Cao, C.; Cai, J. Helical Antimicrobial Sulfono-y-AApeptides. J. Med. Chem. 2015, 58, 4802-4811.

Nimmagadda, A.; Liu, X.; Teng, P.; Su, M.; Li, Y.; Qiao, Q.; Khadka, N. K.; Sun, X.; Pan, J.; Xu, H.; Li, Q.; Cai, J. Polycarbonates with Potent and Selective Antimicrobial Activity toward Gram-Positive Bacteria. Biomacromolecules 2017, 18, 87-95.

Nitrofurantoin

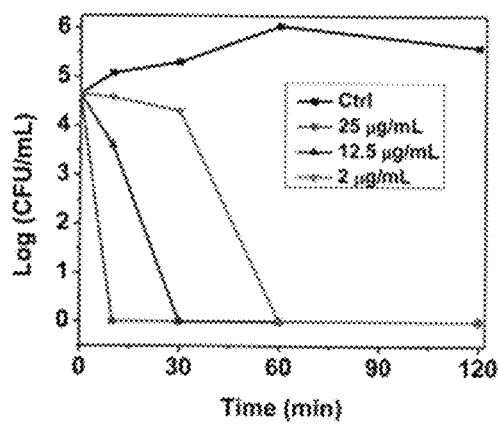
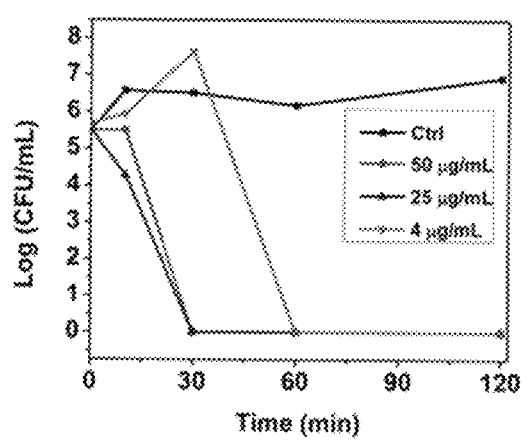
Fig. 5A            Fig. 5B
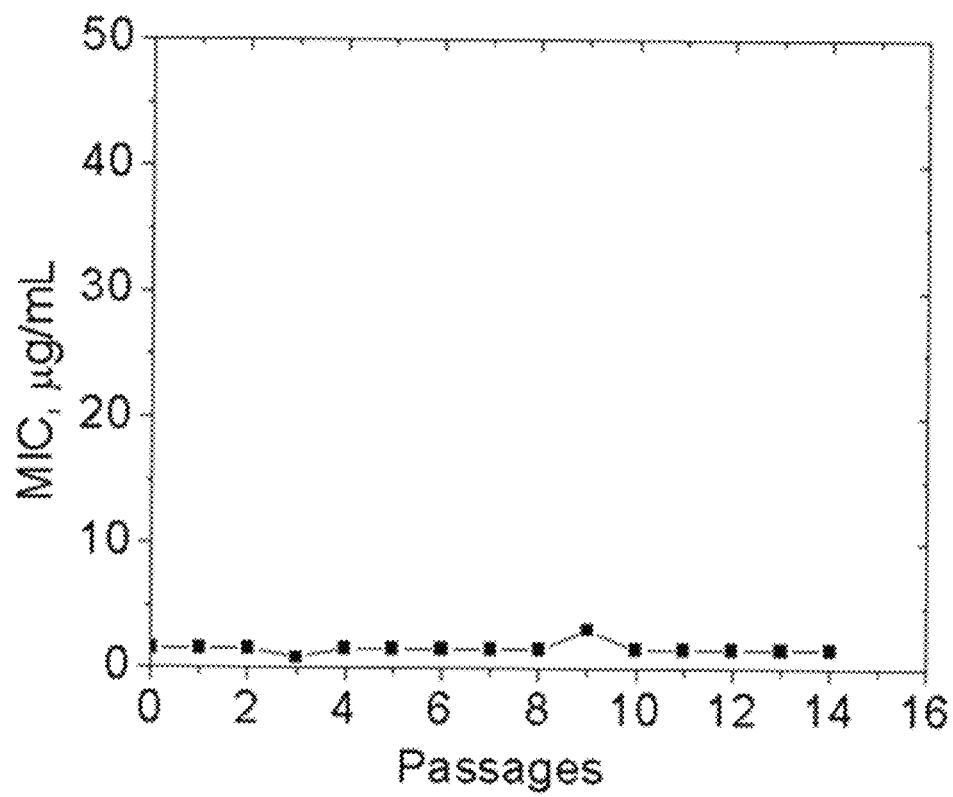
Fig. 6

γ-Lys-BB    γ-Phe-BB

| | DAPI | PI |
|---|---|---|
| MRSA | | |
| MRSA + nitrofurantoin | | |
| E. coli | | |
| E. coli + nitrofurantoin | | |

HYDANTOIN DERIVATIVE COMPOUNDS, METHODS OF USE AND METHODS OF TREATMENT

CROSS-REFERENCE TO RELATED APPLICATIONS

This application claims the benefit of and priority to U.S. Provisional Application Ser. No. 62/426,698, having the title "Cationic Hydantoin Compounds and the Use of", filed on Nov. 28, 2016, the disclosure of which is incorporated herein by reference in its entirety.

STATEMENT REGARDING FEDERALLY SPONSORED RESEARCH OR DEVELOPMENT

This invention was made with government support 1351265 awarded by the National Science Foundation and R01 GM112652 awarded by the National Institutes of Health. The government has certain rights in the invention.

BACKGROUND

Infection caused by drug-resistant bacteria has become one of the greatest threats to public health in the 21st century. Exploration for alternative therapeutic strategies is in a huge demand. One promising approach is to reinvestigate the known antibiotics and design their derivatives, in the hope of identifying novel antibiotic agents that combat antibiotic resistance. Hydantoins, the derivatives of 2,4-imidazolidinedione, have been developed for antibacterial applications for a long time. The mechanism of action for hydantoin derivatives is complex and not well understood, possibly due to a combination of various modes including damage to bacterial DNA, as well as binding to bacterial ribosomes to inhibit synthesis of critical bacterial enzymes, and so on. To date, one hydantoin derivative, nitrofurantoin, has been approved to treat urinary tract infections. As an old antibiotic, it has recently attracted considerable interest due to its low probability of bacterial resistance compared to other conventional antibiotics such as fluoroquinolones, possibly owing to the mixed mechanisms of action of hydantoins. However, hydantoin derivatives including nitrofurantoin generally exhibit only moderate antibacterial activity, which may limit their further application in combating emergent antibiotic resistance. For instance, nitrofurantoin shows a MIC (minimum inhibitory concentration) of 12.5 μg/mL for MRSA, and it is not even active towards P. aeruginosa up to 100 μg/mL.

Another alternative strategy to combat antibiotic resistance is to develop cationic host-defense peptides (HDPs) as potential antibiotic agents. Containing hydrophobic and cationic groups, HDPs and related peptidomimetics such as β-peptides, oligoureas, peptoids, AApeptides, and so forth, are able to selectively interact with negatively charged bacterial membranes, leading to membrane damage and subsequent bacterial cell death. Cationic charges are critical for association of these molecules with bacterial membranes, while hydrophobic groups are of importance for membrane penetration and disruption. HDPs and their derivatives are believed to minimize the probability of bacterial resistance development, as the membrane interaction and disruption is rather biophysical and lack specific membrane targets. It should be noted that besides membrane action, many HDPs could also permeate bacterial membranes and act on bacteria intracellular targets. Indeed, the mixed antibacterial mechanisms are expected to further synergize their ability to overcome bacterial resistance. Despite considerable enthusiasm, HDPs and oligomeric peptidomimetics encounter obstacles for practical applications, including moderate activity and systematic toxicity. In addition, their large molecular weights (normally >1000 Da) and structural complexity lead to tedious synthetic process and high production cost, hampering the therapeutic development of HDPs.

SUMMARY

Embodiments of the present disclosure provide for compounds including hydantoin derivatives, pharmaceutical compounds including hydantoin derivatives, and methods of treatment using hydantoin derivatives.

The present disclosure provides for a hydantoin derivative compound having the following structure:

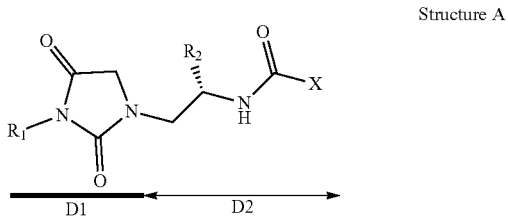

Structure A wherein $D_1$ is a hydantoin core, $D_2$ is a membrane interacting domain, $R_1$ is a hydrophobic group, $R_2$ is a cationic $NH_2$ group, and X is a lipid tail.

Other embodiments provide for pharmaceutical compositions including a hydantoin derivative of Structure A above, or pharmaceutically acceptable salts thereof, and a pharmaceutically acceptable carrier. In Structure A, $D_1$ is a hydantoin core, $D_2$ is a membrane interacting domain, $R_1$ is a hydrophobic group, $R_2$ is a cationic $NH_2$ group, and X is a lipid tail.

Another embodiment includes a method of treating an infection, which can include: delivering, to a subject in need thereof, a composition comprising a therapeutically effective amount of a hydantoin derivative compound, or a pharmaceutically acceptable salt of the hydantoin derivative compound, to treat the infection, wherein the hydantoin derivative compound has Structure A, above. In Structure A, $D_1$ is a hydantoin core, $D_2$ is a membrane interacting domain, $R_1$ is a hydrophobic group, $R_2$ is a cationic $NH_2$ group, and X is a lipid tail.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 5A-B are time-kill plots of compound 22 against MRSA (FIG. 5A) and E. coli (FIG. 5B).

FIG. 6 plots results of a drug resistance study for compound 22.

DETAILED DESCRIPTION

Figure 1:
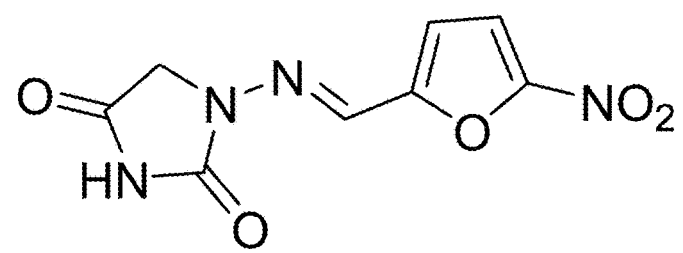
FIG. 1 shows the structure of nitrofurantoin.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, microbiology, pharmacology, and the like, which are within the skill of the art.

The following examples are put forth so as to provide those of ordinary skill in the art with a complete disclosure and description of how to perform the methods and use the compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

The term "substituted" refers to any one or more hydrogens on the designated atom that can be replaced with a selection from the indicated group, provided that the designated atom's normal valence is not exceeded, and that the substitution results in a stable compound. In an embodiment, one or more of the hydrogens can be substituted with a halogen, an alkyl group (unsubstituted or substituted), a cycloalkyl group (unsubstituted or substituted), an aryl group (unsubstituted or substituted), and the like. In particular, the term "substituted," as in "substituted alkyl", "substituted cycloalkyl," "substituted aryl," and the like, means that the substituted group may contain in place of one or more hydrogens a group such as a halogen, an alkyl group (unsubstituted or substituted), a cycloalkyl group (unsubstituted or substituted), an aryl group (unsubstituted or substituted), and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. In an aspect, "alkyl" can include an alkyl group having less than 10 carbon atoms. In an aspect, "alkyl" can include an alkyl group having more than 10 carbon atoms. In an aspect, "alkyl" can include an alkyl group having 5 to 15 carbon atoms. The term "alkyl" can also include straight-chain alkyl groups, branched-chain alkyl groups, cycloalkyl (alicyclic) groups, alkyl-substituted cycloalkyl groups, and cycloalkyl-substituted alkyl groups.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted. In an aspect, a substituted aryl can include with an alkyl group to form a benzyl group for example.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group. The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydia trachomatis, Chlamydia psittaci, Coxiella burnetti,*

*Escherichia coli, Neiserria meningitidis, Neiserria gonorrhea, Haemophilus influenzae, Haemophilus ducreyi,* other *Heemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium*, or any strain or variant thereof. The Gram-positive bacteria may include, but is not limited to, Gram positive Cocci (e.g., *Streptococcus, Staphylococcus*, and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae*, methicillin-resistant *Staphylococcus aureus*, methicillin-resistant *Staphylococcus epidermidis*, Vancomycin-Resistant Enterococci, *Escherichia coli, Klebsiella pneumoniae,* and *Pseudomonas aeruginosa.*

The terms "subject", "individual", or "patient" as used herein are used interchangeably and refer to an animal preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. In a particular embodiment, the mammal is a human. In other embodiments, animals can be treated; the animals can be vertebrates, including both birds and mammals. In aspects of the disclosure, the terms include domestic animals bred for food or as pets, including equines, bovines, sheep, poultry, fish, porcines, canines, felines, and zoo animals, goats, apes (e.g., gorilla or chimpanzee), and rodents such as rats and mice.

In the context of certain aspects of the disclosure, the term "subject" generally refers to an individual who will receive or who has received treatment (e.g., administration of a composition of the disclosure, and optionally one or more other agents) for a condition characterized by an infection or cancer (e.g., leukemia). In certain aspects, a subject may be a healthy subject. Typical subjects for treatment include persons afflicted with or suspected of having or being pre-disposed to a disease disclosed herein, or persons susceptible to, suffering from or that have suffered a disease disclosed herein. A subject may or may not have a genetic predisposition for a disease disclosed herein.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade).

Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the subject being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "diagnosed" as used herein, refers to the recognition of a disease by its signs and symptoms (e.g., resistance to conventional therapies), or genetic analysis, pathological analysis, histological analysis, and the like.

The terms "administering" and "administration" as used herein refer to a process by which a therapeutically effective amount of a compound or composition of the disclosure, or a prodrug of a compound of the disclosure are delivered to a subject for prevention and/or treatment purposes. Compositions are administered in accordance with good medical practices taking into account the subject's clinical condition, the site and method of administration, dosage, patient age, sex, body weight, and other factors known to physicians.

The compounds of the present disclosure may be administered by oral, parenteral (e.g., intramuscular, intraperitoneal, intravenous, ICV, intracisternal injection or infusion, subcutaneous injection, transcutaneous, transdermal, infusion, intra-joint, intra-arteriole, intrathecal, intradermal, intraventricular, intracranial, intraperitoneal, intralesional, intra-articular, intra-peritoneal, intrahepatic, intra-synovial, intrasternal, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The terms "treat" or "treatment" as used herein refer to both therapeutic treatment and prophylactic or preventative measures, where the object is to prevent or slow down (lessen) an undesired physiological change or disorder resulting from the disease. Beneficial or desired clinical results include, but are not limited to, alleviation of symptoms, diminishment of the extent of disease, stabilized (i.e., not worsening) state of disease, and delay or slowing of progression of the symptoms recognized as originating from a stroke. The term "treatment" can also refer to prolonging survival as compared to expected survival if not receiving treatment. Those in need of treatment include those already with the condition or disorder as well as those prone to have the condition or disorder or those in which the condition or disorder is to be prevented or onset delayed.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition (e.g., infection), a disease, or a symptom thereof and/or may be therapeutic in terms of a partial or complete cure for an infection, and/or adverse effect attributable to the infection.

As used herein, "control" can refer to an alternative subject or sample used in an experiment for comparison purposes and included to minimize or distinguish the effect of variables other than an independent variable. A control can be positive or negative.

As used herein, "derivative" can refer to a compound that is based off a lead compound described herein and can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed herein and salts thereof.

As used herein, "biofilms" refer to biological films that develop and persist at interfaces in aqueous environments, especially along the inner walls of conduit material in industrial facilities, in household plumbing systems, on medical implants, or as foci of chronic infections. These biological films are composed of microorganisms embedded in an organic gelatinous structure composed of one or more matrix polymers that are secreted by the resident microorganisms. Biofilms can develop into macroscopic structures several millimeters or centimeters in thickness and can cover large surface areas. Biofilms are also capable of trapping nutrients and particulates that can contribute to their enhanced development and stability. Biofilms can also prevent penetration of antimicrobial agents and therefore, make bacteria within biofilms drug resistant, which leads to persistent infection. Embodiments of the present disclosure can be used to inhibit the growth of a biofilm, where inhibits includes one or more of the following: stopping the growth of the biofilm, killing the biofilm, reducing the size of the biofilm, and the like.

Abbreviations Used MRSA, methicillin-resistant *Staphylococcus aureus*; MRSE, methicillin-resistant *Staphylococcus epidermidis*; VRE, Vancomycin-Resistant Enterococci; E. Coli, *Escherichia coli*; K. P., *Klebsiella pneumoniae*; P. A., *Pseudomonas aeruginosa*; HDPs, host-defense peptides; MIC, minimum inhibitory concentration; DAPI, 4',6-diamidino-2-phenylindole; PI, propidium iodide; PBS, Phosphate-buffered saline; CFU, colony-forming unit; DMF, Dimethylformamide; DCM, dichloromethane; HOBt, Hydroxybenzotriazole; DIPEA, N,N-Diisopropylethylamine; DIC, N,N'-Diisopropylcarbodiimide; TFA, trifluoroacetic acid; HPLC, high performance liquid chromatography.

General Discussion

In accordance with the purpose(s) of the present disclosure, as embodied and broadly described herein, embodiments of the present disclosure, in some aspects, relate to antibiotic compounds. In general, embodiments of the present disclosure provide for compositions including a hydantoin derivative, pharmaceutical compositions including a hydantoin derivative, methods of treatment of a condition (e.g. bacterial infection) or disease, methods of treatment using compositions or pharmaceutical conditions, and the like. In addition, embodiments of the present disclosure can be used to inhibit biofilm growth on a surface or growth of bacteria on a surface.

Hydantoin (imidazolidinedione) derivatives such as nitrofurantoin are small molecules that have aroused considerable interest recently due to their low rate of bacterial resistance. However, their moderate antimicrobial activity may hamper their application combating antibiotic resistance in the long run. Herein the design of bacterial membrane-active hydantoin derivatives are described, from which compounds were identified that show much more potent antimicrobial activity against a panel of clinically relevant Gram-positive and Gram-negative bacterial strains than nitrofurantoin. These compounds are able to act on bacterial membranes, analogous to natural host-defense peptides (HDPs). Additionally, these hydantoin compounds could not only kill bacterial pathogens rapidly, but also prevent the development of methicillin-resistant *Staphylococcus aureus* (MRSA) bacterial resistance under the tested conditions. Also, compound 22 (a lead compound) exhibited in vivo efficacy that is superior to vancomycin by eradicating bacteria and suppressing inflammation caused by MRSA-induced pneumonia on a rat model, demonstrating their promising therapeutic potential.

As described above and herein, examples of the present disclosure describe a new class of hydantoin-based small molecules with membrane activity. It is well known that the existing lipo-antibiotics including marketed drugs daptomycin[37,38] and polymyxin,[39,40] the two "last-resort" antibiotics, all associate and interact with bacterial membranes using their lipid tails. Previous findings also indicate that cationic peptidomimetics with lipidation could kill bacteria with greater potency by disrupting bacterial membranes. Hydantoin compounds bearing cationic groups and lipid tails (FIG. 2, D2) were tested and show activity toward membranes, similar to the mechanism of action of HDPs. As such, they could interact with bacterial membranes and kill bacterial pathogens through bacterial membrane disruption. In addition, as the compounds still contain the hydantoin pharmacophore (FIG. 2, D1), they could also pass bacterial membranes and directly act on the potential targets. The synergistic effect on bacterial killing lead to a new generation of antibiotics with high potency and novel mechanisms, as well as less probability for resistance development. Examples of the present disclosure show that these compounds exhibit much enhanced antimicrobial activity against both Gram-positive and Gram-negative bacteria compared to nitrofurantoin (>50 fold for certain strains), including clinically relevant multidrug resistant bacterial strains.

An embodiment of the present disclosure can be used individually or in combination (e.g., in the same composition or separately) with other antibiotics to treat one or multiple strains of bacteria. Embodiments of the present disclosure can be used as a broad spectrum antibiotic. In an embodiment, compositions of the present disclosure can be used to treat subjects having infections caused by bacteria such as: methicillin-resistant *Staphylococcus aureus*, methicillin-resistant *Staphylococcus epidermidis*, Vancomycin-Resistant Enterococci, *Escherichia coli*, *Klebsiella pneumoniae*, and *Pseudomonas aeruginosa*, or combinations thereof. In addition, embodiments of the present disclosure can be used to inhibit biofilm growth on a surface or growth of bacteria on a surface.

Advantageously, embodiments of the present disclosure can be used to treat both Gram-positive and Gram-negative bacteria. Hydantoin derivatives and pharmaceutically acceptable salts thereof as described herein act on bacterial membranes, thereby combatting the development of antibiotic resistance. Additionally, embodiments of the present disclosure are more potent against clinically relevant bacterial strains than existing compounds such as nitrofurantoin. An exemplary compound, compound 22 as described in the example, also shows excellent in vivo activity toward MRSA-induced pneumonia on a rat model by effectively eradicating MRSA and suppressing lung inflammation caused by pneumonia.

The present disclosure provides for a hydantoin derivative compound and a pharmaceutical compound having Structure A:

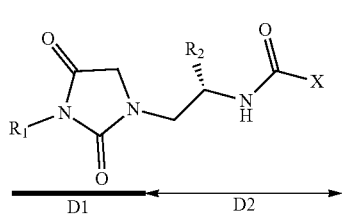

Structure A wherein $D_1$ can be a hydantoin core, $D_2$ can be a membrane interacting domain, $R_1$ can be a hydrophobic group, $R_2$ can be a cationic $NH_2$ group, and X can be a lipid tail.

In an embodiment, $R_1$ can be an alkyl group having 1 to 20 carbon atoms, or in particular (narrower range) 2 to 18 carbons, a cycloalkyl group (e.g., 4 to 12 carbons) or an aryl group (e.g., 4 to 12 carbons), each of which can be substituted or unsubstituted. In an aspect, $R_1$ can be methyl group, ethyl group, propyl group, butyl group, phenyl group, benzyl group, halobenzyl group, and the like.

In an embodiment, X can be a linear or branched alkyl chain having 5-20 carbons, or in particular a 10 to 16 carbons (e.g., ten-carbon to sixteen-carbon chain).

In an embodiment, $R_2$ can be aminobutyrl, aminopentyl, aminohexyl, or aminopropyl.

In an embodiment, the hydantoin derivative compound can have the following structure:

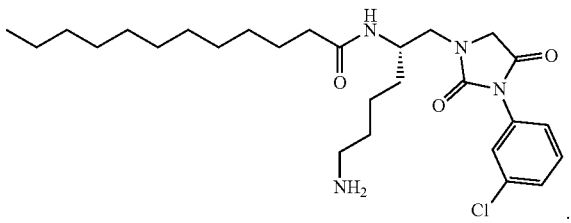 [SMILES: CCCCCCCCCCCC(=O)N[C@@H](CCCCN)CN1CC(=O)N(c2cccc(Cl)c2)C1=O]

In an embodiment, the pharmaceutical composition and the method of treatment (e.g., of an infection such as one directly or indirectly caused by a bacterial infection) includes a therapeutically effective amount of a hydantoin derivative compound, or a pharmaceutically acceptable salt of the hydantoin derivative compound, and a pharmaceutically acceptable carrier, to treat the bacterial infection.

In an embodiment, the method includes treating a subject having an infection, in particular, a bacterial infection. The method can include delivering to a subject in need thereof, a pharmaceutical composition that includes a therapeutically effective amount of a hydantoin derivative compound, or a pharmaceutically acceptable salt of the hydantoin derivative compound, and a pharmaceutically acceptable carrier, to treat the infection.

Embodiments of the hydantoin derivative compound are described herein. In an embodiment the bacterial infections can be caused by for more types of bacteria. In an embodiment, the compounds are broad spectrum antibacterial agents (e.g., an antibiotic towards a wide range of bacteria (e.g., gram positive, gram negative, multiple families of bacteria, multiple types of bacteria, and the like)). In an embodiment, the types of bacteria can include: methicillin-resistant *Staphylococcus aureus*, methicillin-resistant *Staphylococcus epidermidis*, Vancomycin-Resistant Enterococci, *Escherichia coli*, *Klebsiella pneumoniae*, and *Pseudomonas aeruginosa*, or combinations thereof.

It should be noted that the therapeutically effective amount to result in uptake of the hydantoin derivative compound into the subject can depend upon a variety of factors, including for example, the age, body weight, general health, sex, and diet of the subject; the time of administration; the route of administration; the rate of excretion of the specific compound employed; the duration of the treatment; the existence of other drugs used in combination or coincidental with the specific composition employed; the type(s) of bacteria; and like factors well known in the medical arts.

Pharmaceutical Formulations and Routes of Administration

Embodiments of the present disclosure include a hydantoin derivative compound as identified herein and formulated with one or more pharmaceutically acceptable excipients, diluents, carriers and/or adjuvants. In addition, embodiments of the present disclosure include a hydantoin derivative compound formulated with one or more pharmaceutically acceptable auxiliary substances. In particular hydantoin derivative compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the hydantoin derivative compound can be administered to the subject using any means capable of resulting in the desired effect. Thus, the hydantoin derivative compound can be incorporated into a variety of formulations for therapeutic administration. For example, the hydantoin derivative compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the hydantoin derivative compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the hydantoin derivative compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the hydantoin derivative compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the hydantoin derivative compound can be utilized in aerosol formulation to be administered via inhalation. Embodiments of the hydantoin derivative compound can be formulated into pressurized acceptable propellants such as dichlorodifluoromethane, propane, nitrogen and the like.

Furthermore, embodiments of the hydantoin derivative compound can be made into suppositories by mixing with a variety of bases such as emulsifying bases or water-soluble bases. Embodiments of the hydantoin derivative compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the hydantoin derivative compound in a composition as a solution in sterile water, normal saline or another pharmaceutically acceptable carrier.

Embodiments of the hydantoin derivative compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles in accordance with the present disclosure.

In an embodiment, the hydantoin derivative compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the hydantoin derivative compound can be accomplished using any of a variety of refillable, pump systems. Pumps provide consistent, controlled release over time. In some embodiments, the hydantoin derivative compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203, 442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the hydantoin derivative compound) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the hydantoin derivative compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the hydantoin derivative compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the hydantoin derivative compound may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the hydantoin derivative compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the hydantoin derivative compound can be administered to a subject in one or more doses. Those of skill will readily appreciate that dose levels can vary as a function of the specific the hydantoin derivative compound administered, the severity of the symptoms and the susceptibility of the subject to side effects. Preferred dosages for a given compound are readily determinable by those of skill in the art by a variety of means.

In an embodiment, multiple doses of the hydantoin derivative compound are administered. The frequency of administration of the hydantoin derivative compound can vary depending on any of a variety of factors, e.g., severity of the symptoms, and the like. For example, in an embodiment, the hydantoin derivative compound can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the hydantoin derivative compound is administered continuously.

The duration of administration of the hydantoin derivative compound analogue, e.g., the period of time over which the hydantoin derivative compound is administered, can vary, depending on any of a variety of factors, e.g., patient response, etc. For example, the hydantoin derivative compound in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the hydantoin derivative compound) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the hydantoin derivative compound) can be administered in a single dose or in multiple doses.

Embodiments of the hydantoin derivative compound can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the hydantoin derivative compound. Where systemic delivery is desired, administration typically involves invasive or systemically absorbed topical or mucosal administration of pharmaceutical preparations.

In an embodiment, the hydantoin derivative compound can also be delivered to the subject by enteral administration. Enteral routes of administration include, but are not limited to, oral and rectal (e.g., using a suppository) delivery.

Methods of administration of the hydantoin derivative compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Figure 2:
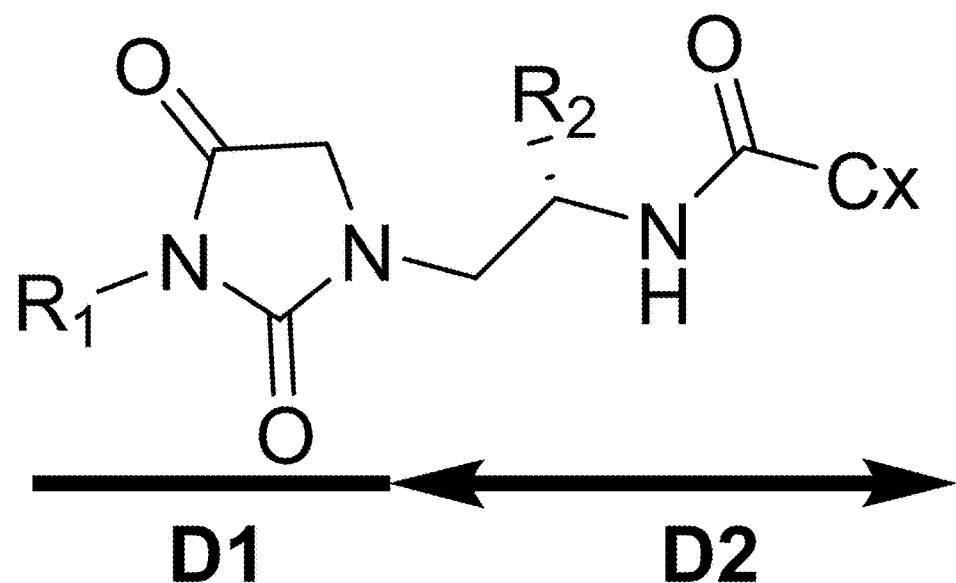
FIG. 2 provides an embodiment of hydantoin compounds with membrane-acting capability. D1 represents the hydantoin core, in which $R_1$ represents a hydrophobic group; D2 represents the membrane interacting domain, in which $R_2$ is the cationic group, and Cx represents a lipid tail.
Figure 3:
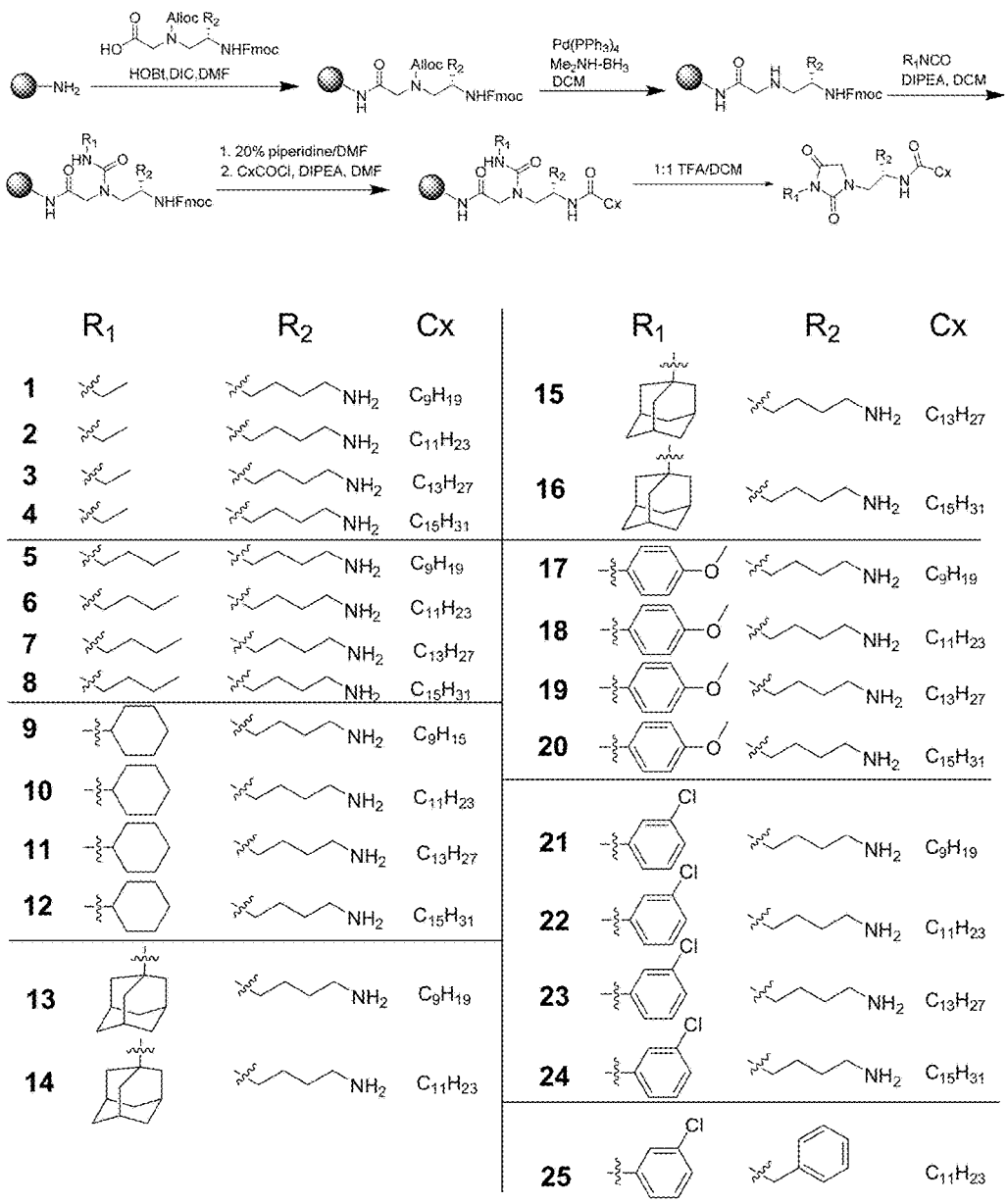
FIG. 3 is an example of the general approach to synthesize cationic lipidated hydantoins and their structures.

The membrane-active hydantoins of the present disclosure were designed in a very straightforward manner, thereby making it possible for convenient optimization and production in the future. As shown in FIG. 2, $R_2$ was designated to be the cationic $NH_2$ group, $R_1$ were hydrophobic groups, and Cx were lipid tails. Note that Cx as indicated in FIG. 2 is the same structure indicated by X in Structure A as described above. The synthesis was also very straightforward (FIG. 3), which allowed a series of compounds to be prepared rapidly on the solid phase. Briefly, the alloc protected γ-AApeptide building block[47,48] bearing the $R_2$ side chain was attached to Rink-amide resin. After the alloc group was removed, the $R_1NCO$ was added to react with the secondary amine to introduce urea functionality. Next, the Fmoc protecting group was removed, followed by reaction with the CxCOCl to introduce the lipid tail. The molecule was then cleaved from the solid support in the presence of 1:1 TFA/DCM, which cyclized spontaneously in situ to yield the desired hydantoin product with good yield.

Subsequently, these cationic hydantoin derivatives were tested for their antimicrobial activity against a panel of Gram-positive and Gram-negative bacteria, including multidrug-resistant clinically relevant strains. The compound 26, nitrofurantoin, exhibited antimicrobial activity against most of bacteria with MICs ranging from 6.25 to 25 μg/mL, which are highly consistent to previously reported antibacterial activity.[11,49] Although nitrofurantoin is the preferred antibiotic to treat bladder and urinal tract infections, as shown above, its antibacterial activity is moderate. It should also be noted that under the tested condition, nitrofurantoin failed to show any activity toward *Pseudomonas aeruginosa*, a notorious Gram-negative strain which could cause severe or even lethal infection.

Table 1. Activity of lipidated cationic hydantoins. Bacteria included in the test were Methicillin-resistant *S. aureus* (MRSA) (ATCC 33591), Methicillin-resistant *S. epidermidis* (MRSE) (RP62A), vancomycin-resistant *E. faecalis* (ATCC 700802), *E. coli* (ATCC 25922), *P. aeruginosa* (ATCC 27853), *K. pneumoniae* (ATCC 13383)[44]. Minimum concentration (MIC) was measured after incubating hydantoins with bacteria for 16 h. Nitrofurantoin (compound 26, in italics) was included in the test as the positive control. The most potent compound 22 is shown in bold.

TABLE 1

Activity of lipidated cationic hydantoins. Bacteria included in the test were Methicillin-resistant *S. aureus* (MRSA) (ATCC 33591), Methicillin-resistant *S. epidermidis* (MRSE) (RP62A), vancomycin-resistant *E. faecalis* (ATCC 700802), *E. coli* (ATCC 25922), *P. aeruginosa* (ATCC 27853), *K. pneumoniae* (ATCC 13383)[44]. Minimum concentration (MIC) was measured after incubating hydantoins with bacteria for 16 h. Nitrofurantoin (compound 26, in *italics*) was included in the test as the positive control. The most potent compound 22 is shown in bold.

| | MIC (μg/mL) | | | | | |
| --- | --- | --- | --- | --- | --- | --- |
| | Gram Positive | | | Gram Negative | | |
| Compound | MRSA | MRSE | VREF | E. coli | P. A. | K. P. |
| 1 | >50 | >50 | >50 | >50 | >50 | >50 |
| 2 | >50 | >50 | >50 | 12.5 | >50 | >50 |
| 3 | 6.25 | 6.25 | 6.25 | 3.12 | 12.5 | 6.25 |
| 4 | 3.12 | 3.12 | 3.12 | 3.12 | >50 | 12.5 |
| 5 | >50 | >50 | >50 | >50 | >50 | >50 |
| 6 | 12.5 | 25 | 25 | 6.25 | 25 | 12.5 |
| 7 | 6.25 | 6.25 | 6.25 | 6.25 | >50 | 12.5 |
| 8 | 6.25 | 6.25 | 6.25 | >50 | >50 | >50 |
| 9 | 25 | >50 | >50 | 12.5 | >50 | 25 |
| 10 | 6.25 | 6.25 | 12.5 | 6.25 | 12.5 | 6.25 |
| 11 | 3.12 | 6.25 | 6.25 | 12.5 | >50 | 6.25 |
| 12 | 3.12 | 25 | 25 | >50 | >50 | >50 |
| 13 | 6.25 | 6.25 | 12.5 | 6.25 | 12.5 | 6.25 |
| 14 | 6.25 | 6.25 | 6.25 | 12.5 | >50 | >50 |
| 15 | 3.12 | 3.15 | 6.25 | >50 | >50 | >50 |
| 16 | >50 | >50 | >50 | >50 | >50 | >50 |
| 17 | >50 | >50 | >50 | >50 | >50 | >50 |
| 18 | 25 | 25 | 25 | 12.5 | 12.5 | 12.5 |
| 19 | 6.25 | 6.25 | 6.25 | 6.25 | >50 | 25 |
| 20 | 3.12 | 6.25 | 6.25 | >50 | >50 | >50 |
| 21 | 6.25 | 6.25 | 12.5 | 6.25 | 6.25 | 6.25 |
| 22 | 0.5 | 0.5 | 0.5 | 1 | 1 | 0.78 |
| 23 | 12.5 | 12.5 | 12.5 | >50 | >50 | >50 |
| 24 | 12.5 | 12.5 | 12.5 | >50 | >50 | >50 |
| 25 | >50 | >50 | >50 | >50 | >50 | >50 |
| *26* | *12.5* | *6.25* | *12.5* | *6.25* | *>50* | *25* |

As the proof of concept, the cationic group $R_2$ from the side chain of lysine was fixed (FIG. 2), and the activity of the compounds explored with respect to the variation of the hydrophobic group $R_1$ and the lipid tail Cx. With the ethyl group for $R_1$ and a C10 decanoic tail for Cx, the compound 1 doesn't exhibit any activity against all tested bacterial strains. It could be due to insufficient hydrophobicity of the ethyl group and short length of the lipid tail, rendering the compound 1 ineffective to interact with bacteria. It is therefore reasonable to observe that the antimicrobial activity of compounds 2 and 3 increases as their lipid tails become longer, which makes them more membrane active. Indeed, compound 3 already has comparable activity to nitrofurantoin against most strains. In addition, it shows an encouraging MIC of 12.5 µg/mL toward *P. aeruginosa*, which is much more potent than nitrofurantoin, suggesting that this class of hydantoin compounds could be further developed. However, it is intriguing that the longer lipid tail doesn't necessarily lead to more potent antimicrobial agents. As seen for 4, which contains the same ethyl group for $R_1$ but a C16 palmitic tail, albeit exhibiting enhanced activity against Gram-positive bacteria, abolishes its activity toward *P. aeruginosa*. It clearly implies that both hydantoin core (D1) and membrane interacting domain (D2) are required for good antimicrobial activity, and a balance of hydrophobicity for $R_1$ and lipid tail length for Cx is needed. With the preliminary studies on this series of ethyl-containing hydantoins, the activity of a few more compounds containing $R_1$ of increased hydrophobicity were tested. With the enhanced rigidity and hydrophobicity, the compounds are generally more active with the same lipid tails. For instance, compound 5, containing the butyl group, doesn't have any antimicrobial activity. In contrast, bearing the cyclohexyl group for $R_1$, compound 9 starts to show activity toward a few bacterial strains. While with the adamantyl group, compound 13 already exhibits decent activity across the panel of bacteria. Similar to compounds 1-4, in each series of compounds bearing the same $R_1$ group, increasing the length of the lipid tail lead to initial enhancement and then detriment in antimicrobial activity. There is a consistent trend that the compounds containing C12 or C14 tail possess the optimal antimicrobial activity. As aromatic groups are frequently identified in vast majority of antibiotic agents, the activity of hydantoins containing phenyl groups as the $R_1$ group were next tested. Although para-methoxybenzyl group-containing compounds 17-20 do not yield better antibiotic agents, hydantoins possessing the meta-chlorobenzyl groups lead to new compounds with potent and broad-spectrum activity. The most potent compound 22 exhibits MICs less than 1 µg/mL against all tested Gram-positive and Gram-negative strains. Compared with nitrofurantoin, it is 25-fold as effective toward MRSA, and at least 50-fold more effective toward *P. aeruginosa*. The impact of the cationic charge $R_2$ on the antimicrobial activity was examined. Surprisingly, replacement of the cationic aminobutyryl group in 22 with the phenyl group gives the highly hydrophobic compound 25, which fails to show any antimicrobial activity. It strongly supports that the cationic charge is of vital importance for antimicrobial activity of this class of hydantoin compounds, possible due to its ability for electrostatic interaction with negatively charged bacterial membranes. In addition, the amphiphilicity of compounds has to be carefully tuned to bear perfect interaction with the bacterial membrane. The overall amphiphilicity of molecules based on HPLC retention time (RT values) were also evaluated. As observed from HPLC data (Table 3), no apparent antibacterial activity display when RT values were less than 26 min (compounds 1, 2, 4, 5, 6, 9, 17, 18, and 25). The antibacterial activity in general increased with increase in RT values from 26 min to 28.4 min (compound 22), then decreased when the RT values were more than 28.4 min. In order to have antibacterial activity, the compounds must have RT values between 26 and 29 min.

TABLE 2

Selectivity of hydantoin compounds. $HC_{50}$ is the hemolytic activity of the compounds. SI is selectivity index, which is the ratio of MIC for MRSA to hemolytic acitivty. Nitrofurantoin (compound 26, in *italics*) was included in the test as the positive control. The most potent compound 22 is shown in bold.

| Compound | MIC of MRSA (µg/mL) | $HC_{50}$ (µg/mL) | SI ($HC_{50}$/MIC) |
|---|---|---|---|
| 3 | 6.25 | 90 | 14.4 |
| 6 | 12.5 | 80 | 6.4 |
| 10 | 6.25 | 100 | 16 |
| 13 | 6.25 | 125 | 20 |
| 18 | 25 | 200 | 8 |
| 21 | 6.25 | 100 | 16 |
| 22 | 0.5 | 95 | 190 |
| *26* | *12.5* | *>200* | *>16* |

In order to evaluate the therapeutic potential of these hydantoin compounds, the selectivity of the lead compounds which exhibited broad-spectrum antimicrobial activity against all tested strains was investigated. As shown in Table 2, these compounds all have better antimicrobial activity than nitrofurantoin 26, while exhibiting limited hemolytic activity. Most noticeably, the most potent compound 22, with much enhanced activity compared with nitrofurantoin, showed excellent selectivity toward MRSA bacteria. In addition to hemolytic activity, the similar selectivity was also observed for mammalian cells, in which 22 has $IC_{50}$s of 90 and 100 µg/mL toward ovarian cancer cells (C13) and colon cancer cells (HCT116), respectively.

Figure 4:
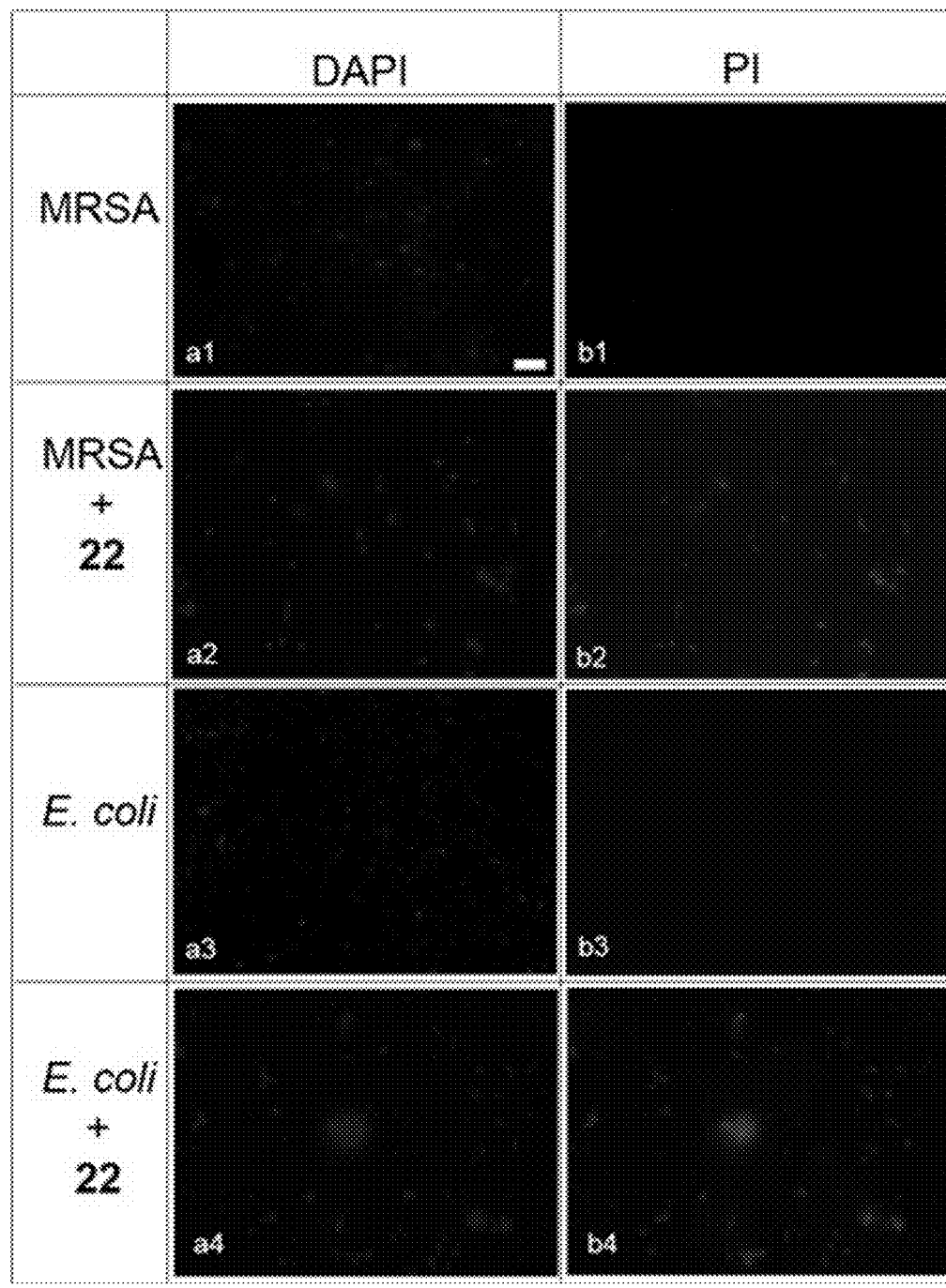
FIG. 4 provides fluorescence micrographs of MRSA and E. coli that were treated or not treated with 5 μg/mL of 22 for 2 h. Cell a1, control, no treatment, DAPI stained; Cell b1, control, no treatment, PI stained. Cell a2, MRSA treatment with 22, DAPI stained; Cell b2, MRSA treatment with 22, PI stained. Cell a3, control, no treatment, DAPI stained; Cell b3, control, no treatment, PI stained. Cell a4, E. coli treatment with 22, DAPI stained; Cell b4, E. coli treatment with 22, PI stained. Scale bar=10 µm.

As aforementioned, the antimicrobial mechanisms of hydantoins are complex and elusive. However, since the compounds developed here were expected to at least possess the mechanism of action analogous to HDPs, their impact on bacterial membranes could be investigated by fluorescent microscopic studies.[44] The most potent compound 22 was thus examined for its ability to compromise bacterial membranes of Gram-positive bacteria MRSA and Gram-negative bacteria *E. coli*.[45] Two dyes, 4',6-diamidino-2-phenylindole (DAPI), and propidium iodide (PI) (FIG. 4), were used to differentiate cells between either intact or damaged membranes. DAPI could permeate intact cell membrane and therefore it shows blue fluorescence regardless of cell viability. In contrast, PI is a DNA intercalator but lack of cell permeability. It only fluoresces in red color when cell membranes are disrupted. As shown in FIG. 4, under the DAPI channel, both MRSA and *E. coli* exhibit blue fluorescence (FIG. 4, cells a1 and a3) in the absence of the compound 22, whereas none of them show fluorescence under the PI channel (FIG. 4, cells b1 and b3), indicating the membranes of these bacteria were intact. However, after bacteria including both MRSA and *E. coli* were incubated with 22 for 2 h, they are able to be stained by both DAPI and PI channels (FIG. 4, cells a2, b2, a4, b4), showing that the membranes of both MRSA and *E. coli* were damaged. Nitrofurantoin was also subjected to the same experiment, however, it did not show any membrane-disruption activity even at 100 µg/mL (FIG. 10), demonstrating that it doesn't inhibit bacterial growth through membrane disruption of bacteria.

HDPs are well known for their ability to eradicate bacteria rapidly, due to their membrane disruptive bactericidal mechanism.[50] It is compelling to know if the newly synthesized hydantoin compounds disclosed herein exhibit similar bacterial killing kinetics. As such, time-kill studies for 22 at different concentrations toward MRSA and *E. coli*, respectively were subsequently carried out. As shown in FIGS. 5A-B, at 25 µg/mL, 22 could completely eradicate MRSA in just 10 min (FIG. 5A). Even at 2.0 µg/mL (4×MIC), MRSA were thoroughly removed in 60 min. Killing *E. coli* is relatively slower, however, all bacteria were still eradicated in 30 min at 25 or 50 µg/mL. At 4.0 µg/mL (4×MIC), *E. coli* could also be completely eradicated in 60 min. It demonstrates that this class of hydantoin compounds could rapidly kill both Gram-positive and Gram-negative pathogens, analogous to HDPs.

One of the most appealing features of HDPs is that they do not readily elicit bacteria resistance, as they disrupt bacterial membranes rather than acting on specific targets.[51] Since compound 22 was designed to be membrane active, in addition to the mechanism of action due to the hydantoin core, we hypothesized that 22 could also prevent the resistance development in bacteria. As such, the drug resistance studies for 22 against MRSA were conducted. 22 were incubated with bacteria at the concentration of half MIC overnight, and the new MIC was measured subsequently. It is intriguing that after 14 passages, MICs of 22 virtually remain unchanged (FIG. 6), which strongly suggests that this class of hydantoin compounds do not readily induce resistance in bacteria, thereby augmenting their potential therapeutic applications.

Figure 7:
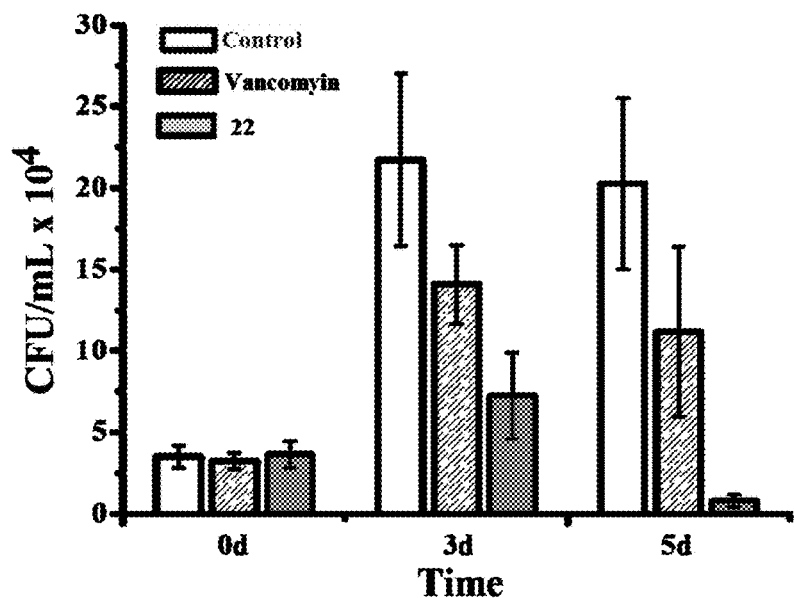
FIG. 7 shows in vivo efficacy of the compound 22 on a rat model bearing MRSA pneumonia bearing. Rats (n=6 per group) were inoculated with 100 µL of $10^6$ CFU/mL MRSA by intratracheal instillation for 24 h (0 d), followed by i.v. injection of 22 (10 mg/kg) in the tail vein and bacterial count after 3 d and 5 d respectively.

One of the major causes of pneumonia is bacterial infection.[52] Hospital-acquired and community-acquired MRSA pneumonia has become more prevalent in recent years and presented significant therapeutic challenges due to its increasing motility.[52] As the hydantoin compounds of the present disclosure exhibited potent in vitro antibacterial activity against both Gram-positive and Gram-negative bacteria including MRSA, it was intriguing to investigate their in vivo activity so as to assess their therapeutic potential. As such, their efficacy was tested on a rat model bearing MRSA pneumonia induced by intratracheal instillation.[41,53] As shown in FIG. 7, the control group, which was treated with PBS only, exhibited high level of MRSA after bacterial inoculation. The slightly decreased quantity of bacteria on day 5 compared with day 3 suggested that rats may fight MRSA through their host immune response.[53] However, the impact on the bacterial clearance was very minimal. Vancomycin, which has long been considered as the "last-resort" antibiotic to treat infections caused by multidrug-resistant Gram-positive pathogens such as MRSA, was included as a positive control. As shown in FIG. 7, on day 3 after the administration of vancomycin, it caused ~30% reduction of bacteria compared with the control. On day 5, the reduction increased ~45%. It indicates that vancomycin could help to clear MRSA from lungs of rats, however, it did exhibit satisfactory efficacy in the inhibition of MRSA proliferation. On the contrary, the compound 22 displayed a much superior in vivo efficacy in the eradication of MRSA bacteria. On day 3 after the treatment of 22, a ~70% reduction in bacteria was observed. On day 5, compared to the control, MRSA was reduced by 96%. The remarkable potency of 22 relative to the control and vancomycin demonstrates its promising therapeutic potential.

Figure 8:
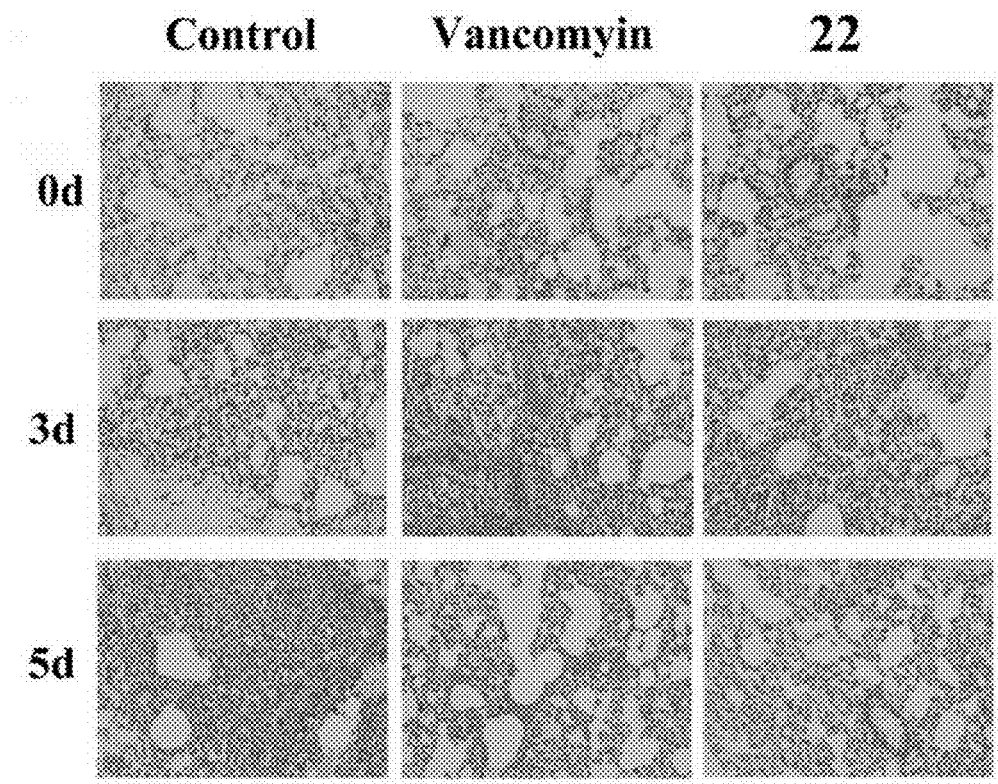
FIG. 8 is an example of a pathological assay based on hematoxylin and eosin (H&E) staining.

Given the findings that 22 could virtually completely eradiate the MRSA bacteria in lungs, pathological analysis was subsequently conducted to find out if 22 could suppress lung inflammation induced by MRSA. As shown in FIG. 8, all three groups (PBS control, vancomycin and 22) demonstrated normal conditions right after MRSA inoculation (0 day), which suggests that the inflammation has not developed in lungs. However, the inflammation in the control group elevated rapidly due to the lack of treatment, as seen for the presence of heavily populated inflammatory cells including monocytes, macrophages, neutrophils, eosinophils, etc (blue spots in H&E staining) on day 5, which is the typical indication of severe lung pneumonia. Rats treated with vancomycin showed alleviated condition due to its ability to inhibit the proliferation of MRSA, which lowered down the inflammation. Remarkably, treatment with the compound 22 exhibited much more significant impact on the suppression of lung inflammation. On day 3, only mild inflammation was observed, whilst on day 5, the inflammation was further mitigated to virtually the normal condition. The findings, consistent with the abovementioned MRSA proliferation studies, strongly suggest that the compound 22 could be superior to vancomycin as a novel therapeutic strategy to treat MRSA pneumonia.

Conclusions

In summary, examples of the present disclosure present a new class of hydantoin derivatives as the potential antibiotic agents. These molecules, bearing cationic charge and hydrophobic lipid tail, were designed to be membrane active in bacterial killing. They exhibited significantly more potent antimicrobial activity against a panel of multidrug-resistant Gram-positive and Gram-negative bacteria than the marketed antibiotic nitrofurantoin, a hydantoin derivative. Although mechanisms of action for hydantoin compounds are known to be complex, our investigation demonstrated that the hydantoin compounds reported here could compromise bacterial membranes, kill bacteria rapidly and do not induce resistance in MRSA even after 14 passages, which is similar to host-defense peptides (HDPs). Moreover, these molecules have also exhibited excellent in vivo efficacy on a rat model bearing MRSA-induced pneumonia, by effectively eradicating MRSA bacteria and suppressing lung inflammation, which is superior to vancomycin. Together with the facile synthesis, these compounds could be an appealing class of antibiotic agents to combat emergent drug-resistance. Further optimization of lead compounds and efficacy studies on other in vivo models are currently underway.

EXPERIMENTAL SECTION

General Information.

Rink amide MBHA resins (0.7 mmol/g, 200-400 mesh) were purchased from Chem-Impex Int'l Inc. Solvents and other chemicals were ordered from either Fisher Scientific or Sigma-Aldrich, and were used without further purification. The $^1$HNMR spectra were obtained on a Varian Inova 400 instrument. The solid phase syntheses of all compounds were carried out in a peptide reaction vessel on a Burrell Wrist-Action shaker. All compounds were analyzed and purified using the Waters Breeze 2 HPLC system under 215 nm of UV detector equipped with both analytical and preparative modules. The desired fractions were lyophilized on a Labcono lyophilizer. The purity of the compounds was determined to be >95% by analytical HPLC. Molar masses of compounds were identified by Agilent Technologies 6540 UHD Accurate-Mass Q-TOF LC/MS spectrometer.

Synthesis of Desired Compounds.

Synthesis of 22 is shown below. The other compounds were synthesized following the similar procedure of 22. 200 mg Rink-amide (MBHA) resin (0.14 mmol) was treated with 3 mL 20% piperidine/DMF (v/v) solution for 15 min (×2) to remove the Fmoc protection group, followed by DMF (2 mL×3) and DCM (2 mL×3) wash. The attachment of the γ-AApeptide building block to the resin was achieved by adding γ-Lys-BB (238 mg, 0.4 mmol), DIC (101 mg, 114 μL, 0.8 mmol), and HOBt (122 mg, 0.8 mmol) in 3 mL DMF to the reaction vessel, and the reaction was allowed to shake at room temperature for 3 h. The solution was drained, and the beads were washed with DCM (3 mL×3) and DMF (3 mL×3). After that, beads were treated with Pd(PPh$_3$)$_4$ (24 mg, 0.02 mmol) and Me$_2$NH.BH$_3$ (70 mg, 1.2 mmol) in 3 mL DCM for 10 min (×2) to remove the alloc protein group, then washed with DCM (3 mL×3) and DMF (3 mL×3). Next, 3-chlorophenyl isocyanate (77 mg, 61 μL, 0.5 mmol) and DIPEA (65 mg, 87 μL, 0.5 mmol) in 3 mL DCM were added to the resin and allowed to react for 30 min at room temperature, and then the solution was drained. After DMF (2 mL×3) and DCM (2 mL×3) wash, beads were treated with 3 mL 20% piperidine/DMF (v/v) solution for 15 min (×2) to remove the Fmoc protection group, followed by wash with DMF (2 mL×3) and DCM (2 mL×3). Subsequently, lauric acid (80 mg, 0.4 mmol), DIC (101 mg, 114 μL, 0.8 mmol), and HOBt (122 mg, 0.8 mmol) in 3 mL DMF were added to the reaction vessel and reacted for 3 h. After the solution was drained, the beads were washed with DMF (2 mL×3) and DCM (2 mL×3), followed by the incubation with 4 mL cocktail of 1:1 TFA:DCM 1:1 (v/v) for 2 h to achieve cleavage and global deprotection of the compound. After the solvent was removed in vacuo, the residue was analyzed and purified on the Waters HPLC system, and the desired fraction was lyophilized to give the pure product 22 which was subsequently characterized by NMR and MS.

(S)—N-(6-amino-1-(3-ethyl-2,4-dioxoimidazolidin-1-yl)hexan-2-yl)decanamide (1)
$^1$HNMR (400 MHz, d$_6$-DMSO) δ 7.73 (brd, 3H), 7.61 (d, J=8.0 Hz, 1H), 4.01 (d, J=6.8 Hz, 1H), 3.81-3.89 (m, 2H), 3.33-3.36 (m, 3H), 3.09 (dd, J=14.0, 4.4 Hz, 1H), 2.65-2.74 (m, 2H), 1.96 (t, J=16.0 Hz, 2H), 1.31-1.49 (m, 6H), 1.10-1.30 (m, 14H), 1.01 (t, J=14.4 Hz, 3H), 0.81 (t, J=16.0 Hz, 3H). $^{13}$CNMR (100 MHz, d$_6$-DMSO) δ 173.0, 170.6, 156.8, 50.3, 46.8, 46.7, 39.1, 35.9, 33.4, 31.6, 31.0, 29.2, 29.1, 29.0, 28.9, 27.0, 25.7, 22.8, 22.5, 14.3, 13.6. HRMS (ESI) C$_{21}$H$_{40}$N$_4$O$_3$ [M+H]$^+$ calc'd=397.3175; found=397.3176.

(S)—N-(6-amino-1-(3-ethyl-2,4-dioxoimidazolidin-1-yl)hexan-2-yl)dodecanamide (2)
$^1$HNMR (400 MHz, d$_6$-DMSO) δ 7.70 (brd, 3H), 7.62 (d, J=8.8 Hz, 1H), 3.80-4.05 (m, 3H), 3.31-3.36 (m, 3H), 3.03 (dd, J=14.0, 4.0 Hz, 1H), 2.67-2.75 (m, 2H), 1.97 (t, J=7.2 Hz, 2H), 1.36-1.49 (m, 6H), 1.10-1.25 (m, 18H), 1.02 (t, J=7.2 Hz, 3H), 0.82 (t, J=6.4 Hz, 3H). $^{13}$CNMR (100 MHz, d$_6$-DMSO) δ 173.0, 170.7, 156.8, 50.3, 46.9, 46.7, 36.0, 33.4, 31.7, 31.0, 29.4, 29.4, 29.3, 29.2, 29.1, 29.0, 27.7, 25.7, 22.8, 22.5, 14.3, 13.7. HRMS (ESI) C$_{23}$H$_{44}$N$_4$O$_3$ [M+H]$^+$ calc'd=425.3485; found=425.3486.

(S)—N-(6-amino-1-(3-ethyl-2,4-dioxoimidazolidin-1-yl)hexan-2-yl)tetradecanamide (3)
$^1$HNMR (400 MHz, d$_6$-DMSO) δ 7.75 (brd, 3H), 7.63 (d, J=8.0 Hz, 1H), 4.02 (d, J=17.2 Hz, 1H), 3.85 (d, J=17.2 Hz, 1H), 3.31-3.33 (m, 3H), 3.03 (dd, J=14.0, 4.0 Hz, 1H), 2.70-2.73 (m, 2H), 1.97 (t, J=7.2 Hz, 2H), 1.29-1.48 (m, 8H), 1.10-1.24 (m, 22H), 1.02 (t, J=7.2 Hz, 3H), 0.82 (t, J=6.4 Hz, 3H). $^{13}$CNMR (100 MHz, d$_6$-DMSO) δ 172.8, 170.7, 156.8, 50.3, 46.9, 46.7, 39.3, 39.1, 36.0, 33.4, 31.7, 31.1, 29.4, 29.3, 29.2, 29.1, 29.0, 27.1, 25.7 22.9, 22.5, 14.4, 13.7. HRMS (ESI) C$_{25}$H$_{48}$N$_4$O$_3$ [M+H]$^+$ calc'd=453.3799; found=453.3800.

(S)—N-(6-amino-1-(3-ethyl-2,4-dioxoimidazolidin-1-yl)hexan-2-yl)palmitamide (4)
$^1$HNMR (400 MHz, d$_6$-DMSO) δ 7.77 (brd, 3H), 7.62 (d, J=9.2 Hz, 1H), 3.79-4.09 (m, 3H), 3.30-3.37 (m, 3H), 3.08 (dd, J=14.0, 4.0 Hz, 1H), 2.65-2.75 (m, 2H), 1.96 (t, J=7.6 Hz, 2H), 1.27-1.53 (m, 6H), 1.03-1.24 (m, 26H), 1.01 (t, J=7.2 Hz, 3H), 0.81 (t, J=6.4 Hz, 3H). $^{13}$CNMR (100 MHz, d$_6$-DMSO) δ 172.8, 170.6, 156.8, 50.3, 46.9, 46.7, 39.1, 36.0, 33.4, 31.7, 31.1, 29.5, 29.3, 29.2, 29.1, 29.1, 27.1, 25.7 22.9, 22.5, 14.4, 13.7. HRMS (ESI) C$_{27}$H$_{52}$N$_4$O$_3$ [M+H]$^+$ calc'd=481.4112; found=481.4110.

(S)—N-(6-amino-1-(3-butyl-2,4-dioxoimidazolidin-1-yl)hexan-2-yl)decanamide (5)
$^1$HNMR (400 MHz, d$_6$-DMSO) δ 7.72 (brd, 3H), 7.62 (d, J=8.8 Hz, 1H), 3.85 (d, J=17.2 Hz, 2H), 3.26-3.45 (m, 3H), 3.00-3.15 (m, 1H), 2.68-2.73 (m, 2H), 1.96 (t, J=14.8 Hz, 2H), 1.32-1.52 (m, 8H), 1.10-1.25 (m, 16H), 0.79-0.83 (m, 6H). $^{13}$CNMR (100 MHz, d$_6$-DMSO) δ 173.0, 170.9, 157.0, 50.2, 46.9, 46.7, 39.2, 38.1, 36.0, 31.7, 31.0, 30.1, 29.3, 29.2, 29.1, 29.0, 27.1, 25.7, 22.8, 22.5, 19.7, 14.3 13.8. HRMS (ESI) C$_{23}$H$_{44}$N$_4$O$_3$ [M+H]$^+$ calc'd=425.3486; found=425.3487.

(S)—N-(6-amino-1-(3-butyl-2,4-dioxoimidazolidin-1-yl)hexan-2-yl)dodecanamide (6)
$^1$HNMR (400 MHz, d$_6$-DMSO) δ 7.75 (brd, 3H), 7.62 (d, J=9.2 Hz, 1H), 4.02 (d, J=17.2 Hz 1H), 3.82-3.94 (m, 2H), 3.25-3.39 (m, 3H), 3.07 (dd, J=14.0, 4.0 Hz, 1H), 2.68-2.74 (m, 2H), 1.96 (t, J=7.6 Hz, 2H), 1.29-1.51 (m, 8H), 1.10-1.22 (m, 20H), 0.79-0.84 (m, 6H). $^{13}$CNMR (100 MHz, d$_6$-DMSO) δ 172.8, 170.8, 156.9, 50.2, 46.9, 46.7, 39.1, 38.1, 36.0, 31.7, 31.1, 30.1, 29.5, 29.4, 29.3, 29.2, 29.1, 27.1, 25.7, 22.9, 22.5, 19.7, 14.4, 13.9. HRMS (ESI) C$_{25}$H$_{48}$N$_4$O$_3$ [M+H]$^+$ calc'd=453.3802; found=453.3803.

(S)—N-(6-amino-1-(3-butyl-2,4-dioxoimidazolidin-1-yl)hexan-2-yl)tetradecanamide (7)
$^1$HNMR (400 MHz, d$_6$-DMSO) δ 7.73 (brd, 3H), 7.62 (d, J=8.8 Hz, 1H), 4.02 (d, J=17.6 Hz 1H), 3.82-3.90 (m, 2H), 3.26-3.38 (m, 3H), 3.07 (dd, J=14.0, 4.0 Hz, 1H), 2.68-2.74 (m, 2H), 1.95 (t, J=7.2 Hz, 2H), 1.30-1.54 (m, 8H), 1.12-1.25 (m, 24H), 0.78-0.84 (m, 6H). $^{13}$CNMR (100 MHz, d$_6$-DMSO) δ 172.8, 170.8, 156.9, 50.2, 46.9, 46.7, 39.1, 38.1, 36.0, 31.7, 31.1, 30.1, 29.5, 29.3, 29.2, 29.1, 27.1, 25.7, 22.9, 22.5, 19.7, 14.3, 13.9. HRMS (ESI) C$_{27}$H$_{52}$N$_4$O$_3$ [M+H]$^+$ calc'd=481.4112; found=481.4111.

(S)—N-(6-amino-1-(3-butyl-2,4-dioxoimidazolidin-1-yl)hexan-2-yl)palmitamide (8)
$^1$HNMR (400 MHz, d$_6$-DMSO) δ 7.77 (brd, 3H), 7.62 (d, J=9.2 Hz, 1H), 4.02 (d, J=17.2 Hz 1H), 3.82-3.89 (m, 2H), 3.25-3.38 (m, 3H), 3.07 (dd, J=13.6, 4.0 Hz, 1H), 2.68-2.73 (m, 2H), 1.95 (t, J=7.2 Hz, 2H), 1.27-1.50 (m, 8H), 1.08-1.22 (m, 28H), 0.79-0.84 (m, 6H). $^{13}$CNMR (100 MHz, d$_6$-DMSO) δ 173.0, 170.8, 157.0, 50.1, 46.9, 46.7, 38.1, 36.0, 31.7, 31.1, 30.1, 29.4, 29.3, 29.2, 29.1, 27.1, 25.7, 22.8, 22.5, 19.7, 14.3, 13.8. HRMS (ESI) C$_{29}$H$_{56}$N$_4$O$_3$ [M+H]$^+$ calc'd=509.4422; found=509.4424.

(S)—N-(6-amino-1-(3-cyclohexyl-2,4-dioxoimidazolidin-1-yl)hexan-2-yl)decanamide (9)
$^1$HNMR (400 MHz, d$_6$-DMSO) δ 7.66 (brd, 3H), 7.59 (d, J=8.8 Hz, 1H), 3.95-3.98 (m, 1H), 3.73-3.85 (m, 2H), 3.61-3.72 (m, 1H), 3.29-3.35 (m, 1H), 3.03-3.08 (m, 1H), 2.65-2.72 (m, 2H), 1.93-1.98 (m, 4H), 1.72 (d, J=12.4 Hz, 2H), 1.28-1.57 (m, 8H), 1.02-1.24 (m, 18H), 0.82 (t, J=6.8 Hz, 3H). $^{13}$CNMR (100 MHz, d$_6$-DMSO) δ 172.9, 170.8, 156.7, 50.9, 49.8, 46.9, 46.6, 36.0, 31.7, 31.0, 29.4, 29.4, 29.2, 29.2, 29.1, 27.1, 25.7, 25.2, 22.8, 22.5, 14.3. HRMS (ESI) C$_{25}$H$_{46}$N$_4$O$_3$ [M+H]$^+$ calc'd=451.3643; found=451.3644.

(S)—N-(6-amino-1-(3-cyclohexyl-2,4-dioxoimidazolidin-1-yl)hexan-2-yl)dodecanamide (10)

$^1$HNMR (400 MHz, d$_6$-DMSO) δ 7.64 (brd, 3H), 7.60 (d, J=9.2 Hz, 1H), 3.95-4.05 (m, 3H), 3.34-3.36 (m, 1H), 3.25 (s, 1H), 3.00-3.09 (m, 1H), 2.71 (s, 2H), 1.90-2.00 (m, 4H), 1.72 (d, J=12.4 Hz, 2H), 1.31-1.59 (m, 8H), 1.00-1.27 (m, 22H), 0.82 (t, J=6.0 Hz, 3H). $^{13}$CNMR (100 MHz, d$_6$-DMSO) δ 173.2, 170.8, 156.7, 50.9, 49.8, 46.9, 46.6, 36.0, 31.7, 31.1, 29.4, 29.4, 29.3, 29.1, 27.1, 25.8, 25.3, 22.5. HRMS (ESI) C$_{27}$H$_{50}$N$_4$O$_3$[M+H]$^+$ calc'd=479.3955; found=479.3956.

(S)—N-(6-amino-1-(3-cyclohexyl-2,4-dioxoimidazolidin-1-yl)hexan-2-yl)tetradecanamide (11)

$^1$HNMR (400 MHz, d$_6$-DMSO) δ 7.72 (brd, 3H), 7.60 (d, J=9.2 Hz, 1H), 3.92-4.00 (m, 1H), 3.61-3.85 (m, 2H), 3.25-3.36 (m, 2H), 3.01-3.10 (m, 1H), 2.68-2.71 (m, 2H), 1.91-2.01 (m, 4H), 1.72 (d, J=12.4 Hz, 2H), 1.30-1.58 (m, 8H), 0.98-1.25 (m, 26H), 0.82 (t, J=6.4 Hz, 3H). $^{13}$CNMR (100 MHz, d$_6$-DMSO) δ 172.7, 170.6, 156.7, 50.9, 49.8, 46.9, 46.6, 39.1, 36.1, 31.7, 31.1, 29.5, 29.4, 29.3, 29.2, 29.1, 27.1, 25.8, 25.2, 22.9, 22.5, 14.3. HRMS (ESI) C$_{29}$H$_{54}$N$_4$O$_3$ [M+H]$^+$ calc'd=507.4269; found=507.4272.

(S)—N-(6-amino-1-(3-cyclohexyl-2,4-dioxoimidazolidin-1-yl)hexan-2-yl)palmitamide (12)

$^1$HNMR (400 MHz, d$_6$-DMSO) δ 7.77 (brd, 3H), 7.61 (d, J=9.2 Hz, 1H), 3.96 (d, J=12.4 Hz, 1H), 3.63-3.81 (m, 2H), 3.28-3.33 (m, 2H), 3.00-3.10 (m, 1H), 2.62-2.75 (m, 2H), 1.91-1.99 (m, 4H), 1.70 (d, J=12.0 Hz, 2H), 1.31-1.59 (m, 8H), 0.99-1.24 (m, 30H), 0.81 (t, J=6.4 Hz, 3H). $^{13}$CNMR (100 MHz, d$_6$-DMSO) δ 173.1, 170.7, 156.7, 51.0, 49.8, 46.9, 46.6, 36.1, 31.7, 31.0, 29.4, 29.3, 29.2, 29.1, 27.0, 25.8, 25.2, 22.8, 22.5, 14.3. HRMS (ESI) C$_{31}$H$_{58}$N$_4$O$_3$ [M+H]$^+$ calc'd=535.4582; found=535.4583.

N—((S)-1-(3-((3R,5R,7R)-adamantan-1-yl)-2,4-dioxoimidazolidin-1-yl)-6-aminohexan-2-yl)decanamide (13)

$^1$HNMR (400 MHz, d$_6$-DMSO) δ 7.76 (brd, 3H), 7.58 (d, J=9.2 Hz, 1H), 3.65-3.88 (m, 3H), 3.26-3.33 (m, 1H), 2.99 (dd, J=14.0, 4.0 Hz, 1H), 2.68-2.74 (m, 2H), 2.27 (d, J=2.4 Hz, 6H), 1.93-2.03 (m, 5H), 1.59 (s, 6H), 1.26-1.51 (m, 6H), 1.15-1.23 (m, 14H), 0.81 (t, J=7.2 Hz, 3H). $^{13}$CNMR (100 MHz, d$_6$-DMSO) δ 172.7, 171.5, 157.3, 59.1, 49.7, 46.7, 46.5, 39.1, 36.2, 36.1, 31.7, 31.2, 29.5, 29.3, 29.2, 27.1, 25.8, 22.9, 22.5, 14.3. HRMS (ESI) C$_{29}$H$_{50}$N$_4$O$_3$[M+H]$^+$ calc'd=503.3955; found=503.3955.

N—((S)-1-(3-((3R,5R,7R)-adamantan-1-yl)-2,4-dioxoimidazolidin-1-yl)-6-aminohexan-2-yl)dodecanamide (14)

$^1$HNMR (400 MHz, d$_6$-DMSO) δ 7.70 (brd, 3H), 7.57 (d, J=9.2 Hz, 1H), 3.85 (d, J=17.2 Hz, 2H), 3.67 (d, J=17.2 Hz, 1H), 3.26-3.33 (m, 1H), 2.99 (dd, J=14.0, 4.0 Hz, 1H), 2.66-2.73 (m, 2H), 2.27 (d, J=2.4 Hz, 6H), 1.95-2.01 (m, 5H), 1.59 (s, 6H), 1.26-1.51 (m, 6H), 1.12-1.23 (m, 18H), 0.81 (t, J=6.4 Hz, 3H). $^{13}$CNMR (100 MHz, d$_6$-DMSO) δ 172.9, 171.5, 157.3, 59.1, 49.6, 46.6, 46.5, 36.2, 36.1, 31.7, 31.2, 29.5, 29.4, 29.3, 29.3, 29.2, 29.1, 27.1, 25.8, 22.9, 22.5 14.3. HRMS (ESI) C$_{31}$H$_{54}$N$_4$O$_3$ [M+H]$^+$ calc'd=531.4269; found=531.4269.

N—((S)-1-(3-((3R,5R,7R)-adamantan-1-yl)-2,4-dioxoimidazolidin-1-yl)-6-aminohexan-2-yl)tetradecanamide (15)

$^1$HNMR (400 MHz, d$_6$-DMSO) δ 6 7.72 (brd, 3H), 7.57 (d, J=9.2 Hz, 1H), 3.85 (d, J=17.2 Hz, 2H), 3.68 (d, J=17.2 Hz, 1H), 3.27-3.34 (m, 1H), 2.99 (dd, J=14.0, 4.0 Hz, 1H), 2.66-2.74 (m, 2H), 2.27 (d, J=2.4 Hz, 6H), 1.94-2.01 (m, 5H), 1.59 (s, 6H), 1.26-1.50 (m, 6H), 1.13-1.22 (m, 22H), 0.81 (t, J=6.4 Hz, 3H). $^{13}$CNMR (100 MHz, d$_6$-DMSO) δ 172.9, 171.5, 157.3, 59.1, 49.6, 46.6, 46.5, 39.1, 36.1, 36.1, 31.7, 31.1, 29.5, 29.4, 29.3, 29.3, 29.2, 29.1, 27.1, 25.8, 22.8, 22.5, 14.3. HRMS (ESI) C$_{33}$H$_{58}$N$_4$O$_3$ [M+H]$^+$ calc'd=559.4578; found=559.4579.

N—((S)-1-(3-((3R,5R,7R)-adamantan-1-yl)-2,4-dioxoimidazolidin-1-yl)-6-aminohexan-2-yl)palmitamide (16)

$^1$HNMR (400 MHz, d$_6$-DMSO) δ 7.63 (brd, 3H), 7.57 (d, J=8.8 Hz, 1H), 3.85 (d, J=17.2 Hz, 2H), 3.68 (d, J=17.2 Hz, 1H), 3.25-3.33 (m, 1H), 2.99 (dd, J=14.0, 4.0 Hz, 1H), 2.68-2.73 (m, 2H), 2.27 (d, J=2.4 Hz, 6H), 1.92-2.02 (m, 5H), 1.60 (s, 6H), 1.24-1.50 (m, 6H), 1.10-1.20 (m, 26H), 0.81 (t, J=7.2 Hz, 3H). $^{13}$CNMR (100 MHz, d$_6$-DMSO) δ 172.9, 171.5, 157.3, 59.1, 49.6, 46.6, 46.4, 39.1, 36.1, 36.1, 31.7, 31.1, 29.5, 29.4, 29.3, 29.3, 29.2, 29.1, 27.1, 25.8, 22.8, 22.5, 14.3. HRMS (ESI) C$_{35}$H$_{62}$N$_4$O$_3$ [M+H]$^+$ calc'd=587.4895; found=587.4897.

(S)—N-(6-amino-1-(3-(4-methoxyphenyl)-2,4-dioxoimidazolidin-1-yl)hexan-2-yl)decanamide (17)

$^1$HNMR (400 MHz, d$_6$-DMSO) δ 7.74 (brd, 3H), 7.68 (d, J=8.8 Hz, 1H), 7.16 (d, J=9.2 Hz, 2H), 6.97 (d, J=8.8 Hz, 2H), 4.18 (d, J=17.2 Hz, 1H), 3.92-4.03 (m, 2H), 3.74 (s, 3H), 3.36-3.42 (m, 1H), 3.17 (dd, J=14.0, 4.0 Hz, 1H), 2.68-2.76 (m, 2H), 1.99 (t, J=7.2 Hz, 2H), 1.29-1.54 (m, 6H), 1.06-1.25 (m, 14H), 0.80 (t, J=6.0 Hz, 3H). $^{13}$CNMR (100 MHz, d$_6$-DMSO) δ 173.1, 170.1, 159.0, 156.2, 128.2, 125.2, 114.4, 55.8, 50.4, 47.2, 46.8, 36.1, 31.7, 31.0, 29.3, 29.1, 27.1, 25.8, 22.9, 22.5, 14.4. HRMS (ESI) C$_{26}$H$_{42}$N$_4$O$_3$ [M+H]$^+$ calc'd=475.3279; found=475.3279.

(S)—N-(6-amino-1-(3-(4-methoxyphenyl)-2,4-dioxoimidazolidin-1-yl)hexan-2-yl)dodecan amide (18)

$^1$HNMR (400 MHz, d$_6$-DMSO) δ 7.78 (brd, 3H), 7.68 (d, J=8.8 Hz, 1H), 7.16 (d, J=9.2 Hz, 2H), 6.96 (d, J=9.2 Hz, 2H), 4.18 (d, J=17.2 Hz, 1H), 3.90-4.03 (m, 2H), 3.74 (s, 3H), 3.37-3.43 (m, 1H), 3.13-3.20 (m, 1H), 2.65-2.80 (m, 2H), 1.99 (t, J=7.2 Hz, 2H), 1.29-1.53 (m, 6H), 1.07-1.24 (m, 18H), 0.80 (t, J=6.0 Hz, 3H). $^{13}$CNMR (100 MHz, d$_6$-DMSO) δ 173.1, 170.0, 158.9, 156.2, 128.2, 125.2, 114.5, 55.7, 50.4, 47.2, 46.8, 39.1, 36.0, 31.7, 31.0, 29.5, 29.4, 29.3, 29.2, 29.1, 27.1, 25.8, 22.8, 22.5, 14.3. HRMS (ESI) C$_{28}$H$_{46}$N$_4$O$_3$ [M+H]$^+$ calc'd=503.3592; found=503.3594.

(S)—N-(6-amino-1-(3-(4-methoxyphenyl)-2,4-dioxoimidazolidin-1-yl)hexan-2-yl)tetradecanamide (19)

$^1$HNMR (400 MHz, d$_6$-DMSO) δ 7.77 (brd, 3H), 7.68 (d, J=9.2 Hz, 1H), 7.16 (d, J=9.2 Hz, 2H), 6.97 (d, J=9.2 Hz, 2H), 4.19 (d, J=17.2 Hz, 1H), 3.91-4.03 (m, 2H), 3.74 (s, 3H), 3.37-3.43 (m, 1H), 3.15-3.21 (m, 1H), 2.70-2.76 (m, 2H), 2.00 (t, J=7.2 Hz, 2H), 1.30-1.57 (m, 6H), 1.10-1.24 (m, 22H), 0.82 (t, J=6.4 Hz, 3H). $^{13}$CNMR (100 MHz, d$_6$-DMSO) δ 172.9, 170.0, 159.0, 156.2, 128.2, 125.3, 114.4, 55.8, 50.4, 47.2, 46.7, 39.1, 36.1, 31.7, 31.1, 29.5, 29.5, 29.4, 29.3, 29.1, 27.1, 25.8, 22.9, 22.5, 14.4. HRMS (ESI) C$_{23}$H$_{44}$N$_4$O$_3$ [M+H]$^+$ calc'd=531.3896; found=531.3894.

(S)—N-(6-amino-1-(3-(4-methoxyphenyl)-2,4-dioxoimidazolidin-1-yl)hexan-2-yl)palmitamide (20)

$^1$HNMR (400 MHz, d$_6$-DMSO) δ 7.76 (brd, 3H), 7.68 (d, J=9.2 Hz, 1H), 7.15 (d, J=9.2 Hz, 2H), 6.96 (d, J=9.2 Hz, 2H), 4.18 (d, J=17.2 Hz, 1H), 3.88-4.04 (m, 2H), 3.73 (s, 3H), 3.39-3.43 (m, 1H), 3.14-3.20 (m, 1H), 2.65-2.78 (m, 2H), 1.99 (t, J=7.2 Hz, 2H), 1.29-1.53 (m, 6H), 1.10-1.24 (m, 26H), 0.81 (t, J=6.4 Hz, 3H). $^{13}$CNMR (100 MHz, d$_6$-DMSO) δ 173.1, 170.0, 158.9, 156.2, 128.2, 125.2, 114.3, 55.7, 50.4, 47.2, 46.7, 39.1, 36.0, 31.7, 31.0, 29.4, 29.4, 29.3, 29.2, 29.1, 27.1, 25.8, 22.8, 22.5, 14.3. HRMS (ESI) C$_{32}$H$_{54}$N$_4$O$_3$ [M+H]$^+$ calc'd=559.4218; found=559.4217.

(S)—N-(6-amino-1-(3-(3-chlorophenyl)-2,4-dioxoimidazolidin-1-yl)hexan-2-yl)decanamide (21)

$^1$HNMR (400 MHz, d$_6$-DMSO) δ 7.74 (brd, 3H), 7.69 (d, J=8.8 Hz, 1H), 7.29-7.50 (m, 4H), 4.01-4.25 (m, 2H), 3.32-3.47 (m, 2H), 3.13-3.21 (m, 1H), 2.73 (s, 2H), 1.99 (t, J=7.2 Hz, 2H), 1.26-1.51 (m, 8H), 1.05-1.21 (m, 12H), 0.78 (t, J=6.4 Hz, 3H). $^{13}$CNMR (100 MHz, d$_6$-DMSO) δ 173.0, 169.6, 155.4, 134.0, 133.2, 130.8, 128.0, 126.3, 125.2, 50.4, 47.3, 46.6, 36.0, 31.7, 31.0, 29.3, 29.1, 27.1, 25.8, 22.9, 22.5, 14.4. HRMS (ESI) C$_{25}$H$_{39}$N$_4$O$_3$ [M+H]$^+$ calc'd=479.2779; found=479.2782.

(S)—N-(6-amino-1-(3-(3-chlorophenyl)-2,4-dioxoimidazolidin-1-yl)hexan-2-yl)dodecanamide (22)

$^1$HNMR (400 MHz, d$_6$-DMSO) δ 7.72 (brd, 3H), 7.31-7.49 (m, 4H), 3.98-4.26 (m, 3H), 3.41-3.45 (m, 1H), 3.19-3.22 (m, 1H), 2.74 (s, 2H), 2.01 (s, 2H), 1.35-1.60 (m, 6H), 1.05-1.34 (m, 18H), 0.83 (t, J=6.8 Hz, 3H). $^{13}$CNMR (100 MHz, d$_6$-DMSO) δ 173.0, 169.8, 155.6, 134.0, 133.2, 130.8, 128.0, 126.3, 125.2, 50.4, 47.3, 46.6, 39.1, 36.0, 31.7, 31.0, 29.5, 29.4, 29.3, 29.3, 29.1, 27.1, 25.8, 22.9, 22.5, 14.4. HRMS (ESI) C$_{27}$H$_{43}$N$_4$O$_3$ [M+H]$^+$ calc'd=507.3092; found=507.3095.

(S)—N-(6-amino-1-(3-(3-chlorophenyl)-2,4-dioxoimidazolidin-1-yl)hexan-2-yl)tetradecanamide (23)

$^1$HNMR (400 MHz, d$_6$-DMSO) δ 7.69-7.73 (m, 1H), 7.67 (brd, 3H), 7.15-7.50 (m, 4H), 3.87-4.28 (m, 3H), 3.34-3.45 (m, 1H), 3.13-3.25 (m, 1H), 2.72 (s, 2H), 1.91-2.15 (m, 2H), 1.27-1.49 (m, 6H), 1.09-1.20 (m, 22H), 0.81 (t, J=6.4 Hz, 3H). $^{13}$CNMR (100 MHz, d$_6$-DMSO) δ 173.2, 169.6, 155.4, 133.9, 133.2, 130.8, 128.0, 126.3, 125.2, 50.3, 47.2, 46.6, 39.1, 36.0, 31.7, 31.0, 29.4, 29.2, 29.2, 29.1, 27.0, 25.8, 22.8, 22.5, 14.3. HRMS (ESI) C$_{29}$H$_{47}$N$_4$O$_3$ [M+H]$^+$ calc'd=535.3408; found=535.3410.

(S)—N-(6-amino-1-(3-(3-chlorophenyl)-2,4-dioxoimidazolidin-1-yl)hexan-2-yl)palmitamide (24)

$^1$HNMR (400 MHz, d$_6$-DMSO) δ 7.67 (d, J=8.8 Hz, 1H), 7.63 (brd, 3H), 7.28-7.49 (m, 4H), 3.90-4.24 (m, 2H), 3.33-3.44 (m, 2H), 3.15-3.21 (m, 1H), 2.72 (s, 2H), 1.99 (m, J=7.6 Hz, 2H), 1.30-1.52 (m, 6H), 1.10-1.22 (m, 26H), 0.81 (t, J=6.4 Hz, 3H). $^{13}$CNMR (100 MHz, d$_6$-DMSO) δ 173.1, 169.6, 155.4, 133.9, 133.2, 130.8, 128.0, 126.3, 125.2, 50.4, 47.2, 46.6, 39.2, 36.0, 31.7, 31.0, 29.4, 29.4, 29.3, 29.2, 29.1, 27.1, 25.8, 22.9, 22.5, 14.4. HRMS (ESI) C$_{31}$H$_{51}$N$_4$O$_3$ [M+H]$^+$ calc'd=563.3722; found=563.3723.

(S)—N-(1-(3-(3-chlorophenyl)-2,4-dioxoimidazolidin-1-yl)-3-phenylpropan-2-yl)dodecanamide (25)

$^1$HNMR (400 MHz, d$_6$-DMSO) δ 7.79 (d, J=9.2 Hz, 1H), 7.36-7.50 (m, 3H), 7.30 (d, J=8.0 Hz, 1H), 7.22 (d, J=4.4 Hz, 4H), 7.10-7.17 (m, 1H), 4.18-4.27 (m, 2H), 4.04 (d, J=17.6 Hz, 1H), 3.47-3.54 (m, 1H), 3.31-3.27 (m, 1H), 2.76-2.82 (m, 1H), 2.60-2.68 (m, 1H), 1.82-1.95 (m, 2H), 1.02-1.32 (m, 18H), 0.81 (t, J=6.8 Hz, 3H). $^{13}$CNMR (100 MHz, d$_6$-DMSO) δ 172.8, 169.6, 155.5, 138.9, 134.0, 133.2, 130.8, 129.4, 128.5, 128.0, 126.5, 126.4, 125.3, 50.4, 48.5, 47.2, 40.8, 37.7, 36.0, 31.7, 29.4, 29.4, 29.2, 29.1, 28.9, 25.7, 22.5, 14.4. HRMS (ESI) C$_{31}$H$_{51}$N$_4$O$_3$ [M+H]$^+$ calc'd=526.2826; found=526.2849.

REFERENCES

1. Levy, S. B.; Marshall, B. Antibacterial resistance worldwide: causes, challenges and responses. *Nat. Med.* 2004, S122-129.
2. Niku-Paavola, M. L.; Laitila, A.; Mattila-Sandholm, T.; Haikara, A. New types of antimicrobial compounds produced by *Lactobacillus plantarum*. *J. Appl. Microbiol.* 1999, 86, 29-35.
3. Ika-Wiani, H.; Yee Yee, T.; David St, C. B.; Roger, W. R. Biological evaluation of certain substituted hydantoins and benzalhydantoins against microbes. *IOP Conf. Ser.: Mater. Sci. Eng.* 2016, 107, 012058.
4. Fujisaki, F.; Toyofuku, K.; Egami, M.; Ishida, S.; Nakamoto, N.; Kashige, N.; Miake, F.; Sumoto, K. Antibacterial activity of some 5-dialkylaminomethylhydantoins and related derivatives. *Chem. Pharm. Bull.* 2013, 61, 1090-1093.
5. Szymanska, E.; Kiec-Kononowicz, K.; Bialecka, A.; Kasprowicz, A. Antimicrobial activity of 5-arylidene aromatic derivatives of hydantoin. Part 2. *Farmaco* 2002, 57, 39-44.
6. van der Stelt, C.; Hofman, P. S.; Nauta, W. T. The effect of alkyl substitution in drugs. 18. Investigation into the synthesis and antimicrobial properties of 1-[(5-nitrofurfurylidene)amino]hydantoin and its 3-substituted products. *A Arzneimittelforschung* 1967, 17, 1331-1333.
7. Tu, Y.; McCalla, D. R. Effect of nitrofurazone on bacterial RNA and ribosome synthesis and on the function of ribosomes. *Chem. Biol. Interact.* 1976, 14, 81-91.
8. Tu, Y.; McCalla, D. R. Effect of activated nitrofurans on DNA. *Biochimi. Biophys. Acta* 1975, 402, 142-149.
9. McOsker, C. C.; Fitzpatrick, P. M. Nitrofurantoin: mechanism of action and implications for resistance development in common uropathogens. *J. Antimicrob. Chemother.* 1994, 33, 23-30.
10. Front MatterA2—Blass, Benjamin E. *Basic Principles of Drug Discovery and Development*, Academic Press: Boston, 2015; p iii.
11. Zhanel, G. G.; Hoban, D. J.; Karlowsky, J. A. Nitrofurantoin is active against vancomycin-resistant enterococci. *Antimicrob. Agents Chemother.* 2001, 45, 324-326.
12. Yu, H.; Pan, L.; Li, P.; Zhang, K.; Lin, X.; Zhang, Y.; Tang, X. Nitrofurantoin enteric pellets with high bioavailability based on aciform crystalline formation by wet milling. *Pharm. Dev. Technol.* 2015, 20, 433-441.
13. Topcu, Y.; Tufan, F.; Bahat, G.; Karan, A. Nitrofurantoin and older women. *Can. Med. Assoc. J.* 2015, 187, 1236.
14. Singh, N.; Gandhi, S.; McArthur, E.; Moist, L.; Jain, A. K.; Liu, A. R.; Sood, M. M.; Garg, A. X. Kidney function and the use of nitrofurantoin to treat urinary tract infections in older women. *Can. Med. Assoc. J.* 2015, 187, 648-656.
15. Zykov, I. N.; Sundsfjord, A.; Smabrekke, L.; Samuelsen, O. The antimicrobial activity of mecillinam, nitrofurantoin, temocillin and fosfomycin and comparative analysis of resistance patterns in a nationwide collection of ESBL-producing *Escherichia coli* in Norway 2010-2011. *Infect. Dis.* (Lond) 2016, 48 (2), 99-107
16. Price, J. R.; Guran, L. A.; Gregory, W. T.; McDonagh, M. S. Nitrofurantoin vs other prophylactic agents in reducing recurrent urinary tract infections in adult women: a systematic review and meta-analysis. *J. Obstet. Gynecol.* 2016, 15, 548-560.
17. McKinnell, J. A.; Stollenwerk, N. S.; Jung, C. W.; Miller, L. G. Nitrofurantoin compares favorably to recommended agents as empirical treatment of uncomplicated urinary tract infections in a decision and cost analysis. *Mayo. Clin. Proc.* 2011, 86, 480-488.
18. Garau, J. Other antimicrobials of interest in the era of extended-spectrum beta-lactamases: fosfomycin, nitrofurantoin and tigecycline. *Clin. Microbiol. Infect.* 2008, 14, 198-202.
19. Otreebska-Machaj, E.; Chevalier, J.; Handzlik, J.; Szymanska, E.; Schabikowski, J.; Boyer, G.; Bolla, J. M.; Kiec-Kononowicz, K.; Pages, J. M.; Alibert, S. Efflux pump blockers in gram-negative bacteria: the new generation of hydantoin based-modulators to improve antibiotic activity. *Front. Microbiol.* 2016, 7, 622.

20. Marinova, P.; Marinov, M.; Kazakova, M.; Feodorova, Y.; Slavchev, A.; Blazheva, D.; Georgiev, D.; Penchev, P.; Sarafian, V.; Stoyanov, N. Study on the synthesis, characterization and bioactivities of 3-methyl-9'-fluorene-spiro-5-hydantoin. *Acta. Chim. Slov.* 2016, 63, 26-32.

21. Handzlik, J.; Szymanska, E.; Chevalier, J.; Otrebska, E.; Kiec-Kononowicz, K.; Pages, J. M.; Alibert, S. Aminealkyl derivatives of hydantoin: new tool to combat resistant bacteria. *Eur. J. Med. Chem.* 2011, 46, 5807-5816.

22. Marr, A. K.; Gooderham, W. J.; Hancock, R. E. Antibacterial peptides for therapeutic use: obstacles and realistic outlook. *Curr. Opin. Pharmacol.* 2006, 6, 468-472.

23. Hancock, R. E.; Sahl, H. G. Antimicrobial and host-defense peptides as new anti-infective therapeutic strategies. *Nat. Biotechnol.* 2006, 24, 1551-1557.

24. Liu, R. H.; Chen, X. Y.; Falk, S. P.; Mowery, B. P.; Karlsson, A. J.; Weisblum, B.; Palecek, S. P.; Masters, K. S.; Gellman, S. H. Structure-activity relationships among antifungal nylon-3 polymers: identification of materials active against drug-resistant strains of *Candida albicans*. *J. Am. Chem. Soc.* 2014, 136, 4333-4342.

25. Choi, H.; Chakraborty, S.; Liu, R. H.; Gellman, S. H.; Weisshaar, J. C. Medium effects on minimum inhibitory concentrations of nylon-3 polymers against *E-coli*. *PloS One* 2014, 9, e104500.

26. Raguse, T. L.; Porter, E. A.; Weisblum, B.; Gellman, S. H. Structure-activity studies of 14-helical antimicrobial beta-peptides: probing the relationship between conformational stability and antimicrobial potency. *J. Am. Chem. Soc.* 2002, 124, 12774-12785.

27. Violette, A.; Fournel, S.; Lamour, K.; Chaloin, O.; Frisch, B.; Briand, J. P.; Monteil, H.; Guichard, G. Mimicking helical antibacterial peptides with nonpeptidic folding oligomers. *Chem. Biol.* 2006, 13, 531-538.

28. Kapoor, R.; Eimerman, P. R.; Hardy, J. W.; Cirillo, J. D.; Contag, C. H.; Barron, A. E. Efficacy of antimicrobial peptoids against *Mycobacterium tuberculosis*. *Antimicrob. Agents Chemother.* 2011, 55 (6), 3058-3062.

29. Ghosh, C.; Manjunath, G. B.; Akkapeddi, P.; Yarlagadda, V.; Hoque, J.; Uppu, D. S.; Konai, M. M.; Haldar, J. Small molecular antibacterial peptoid mimics: the simpler the better! *J. Med. Chem.* 2014, 57, 1428-1436.

30. Teng, P.; Shi, Y.; Sang, P.; Cai, J. γ-AApeptides as a new class of peptidomimetics. *Chem.—Eur. J.* 2016, 22, 5458-5466.

31. Shi, Y.; Teng, P.; Sang, P.; She, F.; Wei, L.; Cai, J. γ-AApeptides: design, structure, and applications. *Acc. Chem. Res.* 2016, 49, 428-441.

32. Fjell, C. D.; Hiss, J. A.; Hancock, R. E. W.; Schneider, G. Designing antimicrobial peptides: form follows function. *Nat. Rev. Drug Discov.* 2012, 11, 37-51.

33. Hancock, R. E. W.; Brown, K. L.; Mookherjee, N. Host defence peptides from invertebrates—emerging antimicrobial strategies. *Immunobiology* 2006, 211, 315-322.

34. Brown, K. L.; Hancock, R. E. W. Cationic host defense (antimicrobial) peptides. *Curr. Opin. Immunol.* 2006, 18, 24-30.

35. Choi, S.; Isaacs, A.; Clements, D.; Liu, D.; Kim, H.; Scott, R. W.; Winkler, J. D.; DeGrado, W. F. De novo design and in vivo activity of conformationally restrained antimicrobial arylamide foldamers. *Proc. Natl. Acad. Sci. U.S.A* 2009, 106, 6968-6973.

36. Chongsiriwatana, N. P.; Patch, J. A.; Czyzewski, A. M.; Dohm, M. T.; Ivankin, A.; Gidalevitz, D.; Zuckermann, R. N.; Barron, A. E. Peptoids that mimic the structure, function, and mechanism of helical antimicrobial peptides. *Proc. Natl. Acad. Sci. U.S.A* 2008, 105, 2794-2799.

37. Wu, G.; Abraham, T.; Rapp, J.; Vastey, F.; Saad, N.; Balmir, E. Daptomycin: evaluation of a high-dose treatment strategy. *Int. J. Antimicrob. Agents* 2011, 38, 192-196.

38. Muraih, J. K.; Pearson, A.; Silverman, J.; Palmer, M. Oligomerization of daptomycin on membranes. *Biochim. Biophys. Acta* 2011, 1808, 1154-1160.

39. Yahav, D.; Farbman, L.; Leibovici, L.; Paul, M. Colistin: new lessons on an old antibiotic. *Clin. Microbiol. Infect.* 2012, 18, 18-29.

40. Nation, R. L.; Li, J. Colistin in the 21st century. *Curr. Opin. Infect. Dis.* 2009, 22, 535-543.

41. Teng, P.; Huo, D.; Nimmagadda, A.; Wu, J.; She, F.; Su, M.; Lin, X.; Yan, J.; Cao, A.; Xi, C.; Hu, Y.; Cai, J. Small antimicrobial agents based on acylated reduced amide scaffold. *J. Med. Chem.* 2016, 59, 7877-7887.

42. Li, Y.; Smith, C.; Wu, H.; Teng, P.; Shi, Y.; Padhee, S.; Jones, T.; Nguyen, A. M.; Cao, C.; Yin, H.; Cai, J. Short antimicrobial lipo-alpha/gamma-AA hybrid peptides. *ChemBioChem* 2014, 15, 2275-2280.

43. Padhee, S.; Li, Y.; Cai, J. Activity of lipo-cyclic gamma-AApeptides against biofilms of *Staphylococcus epidermidis* and *Pseudomonas aeruginosa*. *Bioorg. Med. Chem. Lett.* 2015, 25, 2565-2569.

44. Li, Y.; Smith, C.; Wu, H.; Padhee, S.; Manoj, N.; Cardiello, J.; Qiao, Q.; Cao, C.; Yin, H.; Cai, J. Lipidated cyclic γ-AApeptides display both antimicrobial and anti-inflammatory activity. *ACS Chem. Biol.* 2014, 9, 211-217.

45. Niu, Y.; Padhee, S.; Wu, H.; Bai, G.; Qiao, Q.; Hu, Y.; Harrington, L.; Burda, W. N.; Shaw, L. N.; Cao, C.; Cai, J. Lipo-gamma-AApeptides as a new class of potent and broad-spectrum antimicrobial agents. *J. Med. Chem.* 2012, 55, 4003-4009.

46. Hu, Y.; Amin, M. N.; Padhee, S.; Wang, R. E.; Qiao, Q.; Bai, G.; Li, Y.; Mathew, A.; Cao, C.; Cai, J. Lipidated peptidomimetics with improved antimicrobial activity. *ACS Med. Chem. Lett.* 2012, 3, 683-686.

47. Wu, H. F.; She, F. Y.; Gao, W. Y.; Prince, A.; Li, Y. Q.; Wei, L. L.; Mercer, A.; Wojtas, L.; Ma, S. Q.; Cai, J. F. The synthesis of head-to-tail cyclic sulfono-gamma-AApeptides. *Org. Biomol. Chem.* 2015, 13, 672-676.

48. Wu, H. F.; Teng, P.; Cai, J. F. Rapid access to multiple classes of peptidomimetics from common gamma-AApeptide building blocks. *Eur. J. Org. Chem.* 2014, 2014, 1760-1765.

49. Chamberlain, R. E. Chemotherapeutic properties of prominent nitrofurans. *J. Antimicrob. Chemother.* 1976, 2 (4), 325-336.

50. Ge, Y.; MacDonald, D. L.; Holroyd, K. J.; Thornsberry, C.; Wexler, H.; Zasloff, M. In vitro antibacterial properties of pexiganan, an analog of magainin. *Antimicrob. Agents Chemother.* 1999, 43, 782-788.

51. Bowdish, D. M. E.; Davidson, D. J.; Lau, Y. E.; Lee, K.; Scott, M. G.; Hancock, R. E. W. Impact of LL-37 on anti-infective immunity. *J. Leukoc. Biol.* 2005, 77, 451-459.

52. Rubinstein, E.; Kollef, M. H.; Nathwani, D. Pneumonia caused by methicillin-resistant *Staphylococcus aureus*. *Clin. Infect. Dis.* 2008, 46, S378-385.

53. Huo, D.; Ding, J.; Cui, Y. X.; Xia, L. Y.; Li, H.; He, J.; Zhou, Z. Y.; Wang, H. W.; Hu, Y. X-ray CT and pneumonia inhibition properties of gold-silver nanoparticles for targeting MRSA induced pneumonia. *Biomaterials* 2014, 35, 7032-7041.

Experimental Data
Synthesis of γ-AApeptide Building Blocks

Figures 9, 10:
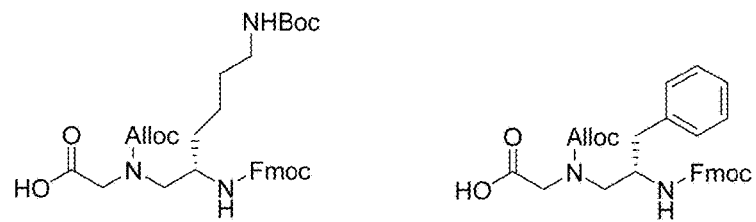
FIG. 9 shows γ-AApeptide building blocks used in the present disclosure.
FIG. 10 provides examples of fluorescence micrographs of MRSA and E. coli that were treated or not treated with 100 µg/mL of nitrofurantoin for 2 h.

Both γ-AApeptide building blocks shown in FIG. 9 were used in the synthesis of hydantoin compounds; their synthetic procedure was reported previously.[1]

Minimum Inhibitory Concentrations (MICs) Assay.[2]

All compounds were tested against six different bacteria strains: methicillin-resistant *S. aureus* (MRSA, ATCC 33591), *E. coli* (ATCC 25922), methicillin-resistant *S. epidermidis* (MRSE, RP62A), *K. pneumoniae* (ATCC 13383), vancomycin-resistant *Enterococcus faecalis* (VREF, ATCC 700802), *P. aeruginosa* (ATCC 27853). One colony of each bacteria was inoculated in 4 mL TSB buffer at 37° C. overnight, which was then diluted 100 times, and the bacteria were allowed to grow to the mid-logarithmic phase. 50 µL hydantoin compounds in 2-fold serial dilution of TSB were added in the 96-well plate, then 50 µL diluted bacterial in TSB medium ($1 \times 10^6$ CFU/mL) was added to each well. After 16 h of incubation at 37° C., the absorption at 600 nm wavelength on a Biotek Synergy HT microtiter plate reader was recorded. Minimum inhibitory concentrations were determined as the lowest concentrations that inhibited bacteria growth completely.

Time Kill Assay.[2]

Bacteria MRSA (Gram-positive) and *E. coli* (Gram-negative) suspensions were allowed to grow at 37° C. to the mid-logarithmic phase, and diluted to $1 \times 10^6$ CFU/mL, then incubated with the compound 22 at the concentration of 50, 25, 12.5 µg/mL at 10 min, 30 min, 1 h and 2 h, respectively. The resulted mixture was then diluted by $10^2$ to $10^4$ fold, from which 100 µL was spread on the TSB agar plate. The Number of bacteria colonies was counted after 20 h of incubation at 37° C.

Drug Resistance Assay.[3]

The lead compound 22 was chosen for drug resistance studies. Briefly, after its MIC against MRSA was determined, the bacteria solution from the well of the ½ MIC was withdrawn and diluted to $1 \times 10^6$ CFU/mL for the next MIC measurement. The measurement was repeated for 14 passages.

Hemolytic Assay.[2]

Fresh red blood cells (RBCs) of mice were washed with 1×PBS buffer and centrifuged 10 min at 3500 rpm for 3 times until the supernatant was clear, then RBCs were diluted into 5% v/v suspension in 1×PBS. 50 µL compounds in PBS were 2-fold serially diluted in a 96-well plate, and incubated with 50 µL RBCs suspension for 1 h at 37° C. The mixture was then centrifuged for 10 min at 3500 rpm. Subsequently, 30 µL of the supernatant was added to 100 µL PBS, then the absorbance of mixture was read on a Biotek Synergy HT plate reader at 540 nm. The hemolytic activity was calculated by the formula % hemolysis=($Abs_{sample}$–$Abs_{PBS}$)/($Abs_{Triton}$–$Abs_{PBS}$)×100%. 1% Triton X-100 were used as the positive control and 1×PBS buffer was used as the negative control.

Fluorescence Microscopy.[2]

Both propidium iodide (PI) and 4',6'-diamidino-2-phenylindole dihydrochloride (DAPI) fluorescent dyes were used in the studies to determine the ability of the compound 22 to compromise the membranes of MRSA and *E. coli*, respectively. In brief, bacterial suspensions were incubated at 37° C. to the mid-logarithmic phase and then diluted by 100 fold, followed by incubation with 5 µg/mL of 22 or 100 µg/mL of nitrofurantoin for 2 h at 37° C. After centrifugation for 15 min at 5000 rpm, cell pellets were washed with 1×PBS buffer, and incubated with PI (5 µg/mL) for 15 min on ice in the dark, then washed 2 times with PBS. Then the cell pellets were incubated with DAPI (10 µg/mL) in the similar way. The pellets were then diluted in 100 µL PBS, and 10-20 µL of the suspension was applied on chamber slides and observed under Zeiss Axio Image Zloptical microscope using 100× oil-immersion objective.

In Vivo Study

The Rat Model of MRSA-Induced Pneumonia.[4,5]

The protocol of animal studies was approved by the institutional committee for animal care of Nanjing University, and the experiments were conducted following the regulation of the National Ministry of Health of China. In Brief, male Wistar rats (6-8 weeks, ~200 g in average weight) were subjected to fast for 12 h. Next, rats were anesthetized by intraperitoneal administration of 0.35 g/kg of chloral hydrate. To induce MRSA pneumonia, the trachea of rats were exposed, to which 100 µL PBS containing $2 \times 10^6$ CFU/mL MRSA in PBS was slowly injected. The rats were retained upright for 1 min, and the cut was sealed. The MRSA infection was allowed to develop for 24 h.

Bronchoalveolar Lavage (BAL) Assay.

The assay was carried out to quantify the bacteria in the lungs of rats. The thorax of rats was opened, and the lungs were collected in each group at different time points. Then the lungs were malleated and homogenized by a glass homogenizer, and diluted with PBS to the determined volume. After that, 10 µL solution was picked up, diluted with PBS by 100-fold, and daubed on the isolation medium. Bacteria were counted in each sample after incubation for 24 h at 37° C., from which the number of bacteria (colonies/g tissue) was calculated.

Pathological Analysis:

The hydantoin compound 22 or vancomycin were used as antibiotics in the study. In brief, a dose of 10 mg/kg of the drug was injected to the tested rats intravenously. On the day of 3 and 5, rats were sacrificed, and lung sections were stained with hematoxylin and eosin (H&E), and their morphology was investigated under a light microscope at 100× magnification. The existence (indicated by the infiltration of neutrophils) and the extent of possible inflammatory response (indicated by the integrity of the alveolar structure and endothelium cilium) were recorded from at least five randomly picked sections by an experienced physician.

HPLC Analysis of Compounds 1-25.

TABLE 3

HPLC purities (under 215 nm) and retention time of compounds 1-25.

| Compound Name | Retention time (min) | Purity (%) |
| --- | --- | --- |
| 1 | 21.81 | 98.7 |
| 2 | 24.75 | 99.0 |
| 3 | 28.71 | 96.7 |
| 4 | 31.98 | 99.9 |
| 5 | 23.52 | 98.6 |
| 6 | 26.45 | 99.2 |
| 7 | 30.78 | 98.9 |
| 8 | 34.39 | 95.7 |
| 9 | 25.30 | 97.9 |
| 10 | 28.75 | 99.6 |
| 11 | 32.26 | 98.2 |
| 12 | 38.19 | 97.0 |
| 13 | 28.98 | 97.4 |
| 14 | 32.16 | 98.4 |
| 15 | 37.00 | 98.6 |
| 16 | 41.80 | 98.9 |
| 17 | 22.81 | 97.7 |
| 18 | 26.20 | 99.1 |
| 19 | 33.53 | 99.1 |
| 20 | 32.97 | 97.6 |
| 21 | 24.11 | 99.5 |

TABLE 3-continued

HPLC purities (under 215 nm) and retention time of compounds 1-25.

| Compound Name | Retention time (min) | Purity (%) |
|---|---|---|
| 22 | 28.44 | 97.9 |
| 23 | 31.59 | 98.5 |
| 24 | 35.38 | 96.2 |
| 25 | 25.20 | 95.2 |

EXPERIMENTAL DATA REFERENCES

1. Niu, Y.; Hu, Y.; Li, X.; Chen, J.; Cai, J. [gamma]-AApeptides: design, synthesis and evaluation. *New J. Chem.* 2011, 35, 542-545.
2. Li, Y.; Wu, H.; Teng, P.; Bai, G.; Lin, X.; Zuo, X.; Cao, C.; Cai, J. Helical Antimicrobial Sulfono-γ-AApeptides. *J. Med. Chem.* 2015, 58, 4802-4811.
3. Nimmagadda, A.; Liu, X.; Teng, P.; Su, M.; Li, Y.; Qiao, Q.; Khadka, N. K.; Sun, X.; Pan, J.; Xu, H.; Li, Q.; Cai, J. Polycarbonates with Potent and Selective Antimicrobial Activity toward Gram-Positive Bacteria. *Biomacromolecules* 2017, 18, 87-95.
4. Huo, D.; Ding, J.; Cui, Y. X.; Xia, L. Y.; Li, H.; He, J.; Zhou, Z. Y.; Wang, H. W.; Hu, Y. X-ray CT and pneumonia inhibition properties of gold-silver nanoparticles for targeting MRSA induced pneumonia. *Biomaterials* 2014, 35, 7032-7041.
5. Teng, P.; Huo, D.; Nimmagadda, A.; Wu, J.; She, F.; Su, M.; Lin, X.; Yan, J.; Cao, A.; Xi, C.; Hu, Y.; Cai, J. Small Antimicrobial Agents Based on Acylated Reduced Amide Scaffold. *J. Med. Chem.* 2016, 59, 7877-7887.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A hydantoin derivative compound having the following structure:

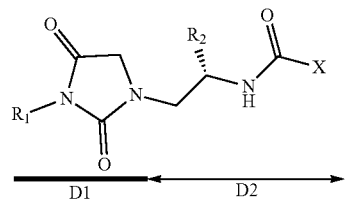

Structure A wherein $D_1$ is a hydantoin core, $D_2$ is a membrane interacting domain, $R_1$ is a hydrophobic group, $R_2$ is selected from the group consisting of a $NH_2$ group, an aminobutyl group, an aminopentyl group, an aminohexyl group, and an aminopropyl group, and X is a lipid tail.

2. The hydantoin derivative compound of claim 1, wherein the lipid tail X is a 5 to 15 carbon alkyl group.

3. The hydantoin derivative compound of claim 2, wherein the lipid tail X is selected from a 10 to 12 carbon linear alkyl group.

4. The hydantoin derivative compound of claim 2, wherein $R_1$ is an alkyl group, aryl group, or a cycloalkyl group, each of which is substituted or unsubstituted.

5. The hydantoin derivative compound of claim 4, wherein $R_1$ is an ethyl group, a phenyl group, meta-chlorobenzyl, indole, biphenyl, terphenyl, or 6-chloro indole.

6. The hydantoin derivative compound of claim 2, wherein the hydantoin derivative compound has the following structure:

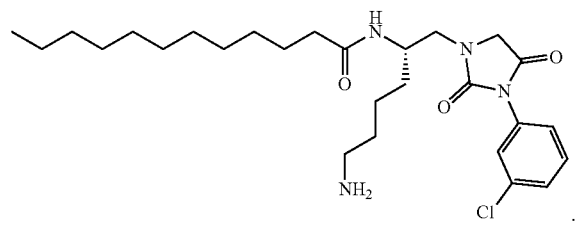 [SMILES: CCCCCCCCCCCC(=O)N[C@@H](CCCCN)CN1CC(=O)N(c2cccc(Cl)c2)C1=O]

7. A pharmaceutical composition comprising:
a hydantoin derivative compound, or a pharmaceutically acceptable salt of the hydantoin derivative compound, having the following structure:

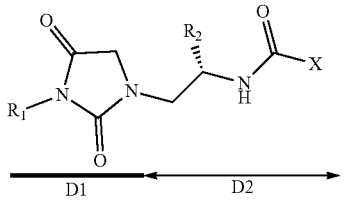

Structure A wherein $D_1$ is a hydantoin core, $D_2$ is a membrane interacting domain, $R_1$ is a hydrophobic group, $R_2$ is selected from the group consisting of a $NH_2$ group, an aminobutyl group, an aminopentyl group, an aminohexyl group, and an aminopropyl group, and X is a lipid tail;
and a pharmaceutically acceptable carrier.

8. The pharmaceutical composition of claim 7, wherein the lipid tail X is a 5 to 15 carbon alkyl group.

9. The pharmaceutical composition of claim 7, wherein the lipid tail X is selected from a 10 to 12 carbon linear alkyl group.

10. The pharmaceutical composition of claim 7, wherein $R_1$ is an alkyl group, aryl group, or a cycloalkyl group, each of which is substituted or unsubstituted.

11. The pharmaceutical composition of claim 10, wherein $R_1$ is an ethyl group, a phenyl group, meta-chlorobenzyl, indole, biphenyl, terphenyl, or 6-chloro indole.

12. The pharmaceutical composition of claim 7, wherein the hydantoin derivative compound has the following structure:

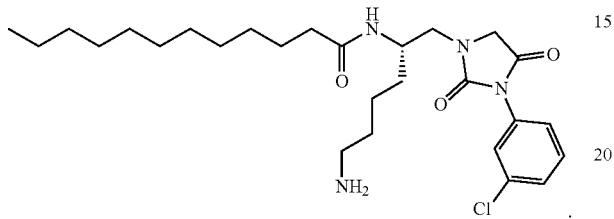

* * * * *